United States Patent
Karlsson et al.

(10) Patent No.: US 10,882,917 B2
(45) Date of Patent: Jan. 5, 2021

(54) ANTI-TUMOR AGENTS AND METHODS OF USE

(71) Applicant: The Rockefeller University, New York, NY (US)

(72) Inventors: Mikael Karlsson, Stockholm (SE); Jeffrey V. Ravetch, New York, NY (US)

(73) Assignee: The Rockefeller University, New Yor, NY (US)

(*) Notice: Subject to any disclaimer, the term of this patent is extended or adjusted under 35 U.S.C. 154(b) by 417 days.

(21) Appl. No.: 15/578,362

(22) PCT Filed: Jun. 1, 2016

(86) PCT No.: PCT/US2016/035237
§ 371 (c)(1),
(2) Date: Nov. 30, 2017

(87) PCT Pub. No.: WO2016/196612
PCT Pub. Date: Dec. 8, 2016

(65) Prior Publication Data
US 2018/0171021 A1 Jun. 21, 2018

Related U.S. Application Data

(60) Provisional application No. 62/169,920, filed on Jun. 2, 2015, provisional application No. 62/169,119, filed on Jun. 1, 2015.

(51) Int. Cl.
| | | |
|---|---|---|
| *C07K 16/28* | (2006.01) | |
| *C07K 16/30* | (2006.01) | |
| *C07K 16/40* | (2006.01) | |
| *A61K 39/00* | (2006.01) | |

(52) U.S. Cl.
CPC ............. *C07K 16/30* (2013.01); *C07K 16/28* (2013.01); *C07K 16/2818* (2013.01); *C07K 16/40* (2013.01); *A61K 2039/505* (2013.01); *A61K 2039/507* (2013.01); *C07K 2317/21* (2013.01); *C07K 2317/24* (2013.01); *C07K 2317/52* (2013.01); *C07K 2317/71* (2013.01); *C07K 2317/92* (2013.01)

(58) Field of Classification Search
None
See application file for complete search history.

(56) References Cited

U.S. PATENT DOCUMENTS

| | | |
|---|---|---|
| 2010/0227415 A1 | 9/2010 | Winqvist et al. |
| 2011/0059054 A1 | 3/2011 | Mule et al. |
| 2011/0104104 A1 | 5/2011 | Metzger et al. |

FOREIGN PATENT DOCUMENTS

| | | | |
|---|---|---|---|
| WO | 2009114547 A2 | | 9/2009 |
| WO | WO2012066058 | * | 5/2012 |
| WO | 2014012933 A1 | | 1/2014 |

OTHER PUBLICATIONS

Almagro & Fransson, Frontiers in Bioscience 2008; 13:1619-33 (Year: 2008).*
De Genst et al., Dev Comp Immunol 2006; 30:187-98 (Year: 2006).*
Yoshinaga et al., J. Biochem 2008; 143:593-601. (Year: 2008).*
Georgoudaki et al., "Reprogramming Tumor-Associated Macrophages by Antibody Targeting Inhibits Cancer Progression and Metastasis," Cell Reports (2016); 15:2000-2011.
Matsushita et al., "Targeting MARCO can lead to enhanced dendritic cell motility and anti-melanoma activity," Cancer Immunol. Immunother. (2010); 59:875-884.
Palecanda et al., "Role of the scavenger receptor MARCO in alveolar macrophage binding of unopsonized environmental particles," (May 3, 1999); 189:1497-506.

* cited by examiner

*Primary Examiner* — Meera Natarajan
(74) *Attorney, Agent, or Firm* — Fox Rothschild LLP

(57) ABSTRACT

The present invention relates to anti-tumor agents that target certain tumor-associated macrophages. Also disclosed are methods of using such agents in treatment of cancer.

8 Claims, 7 Drawing Sheets

Specification includes a Sequence Listing.

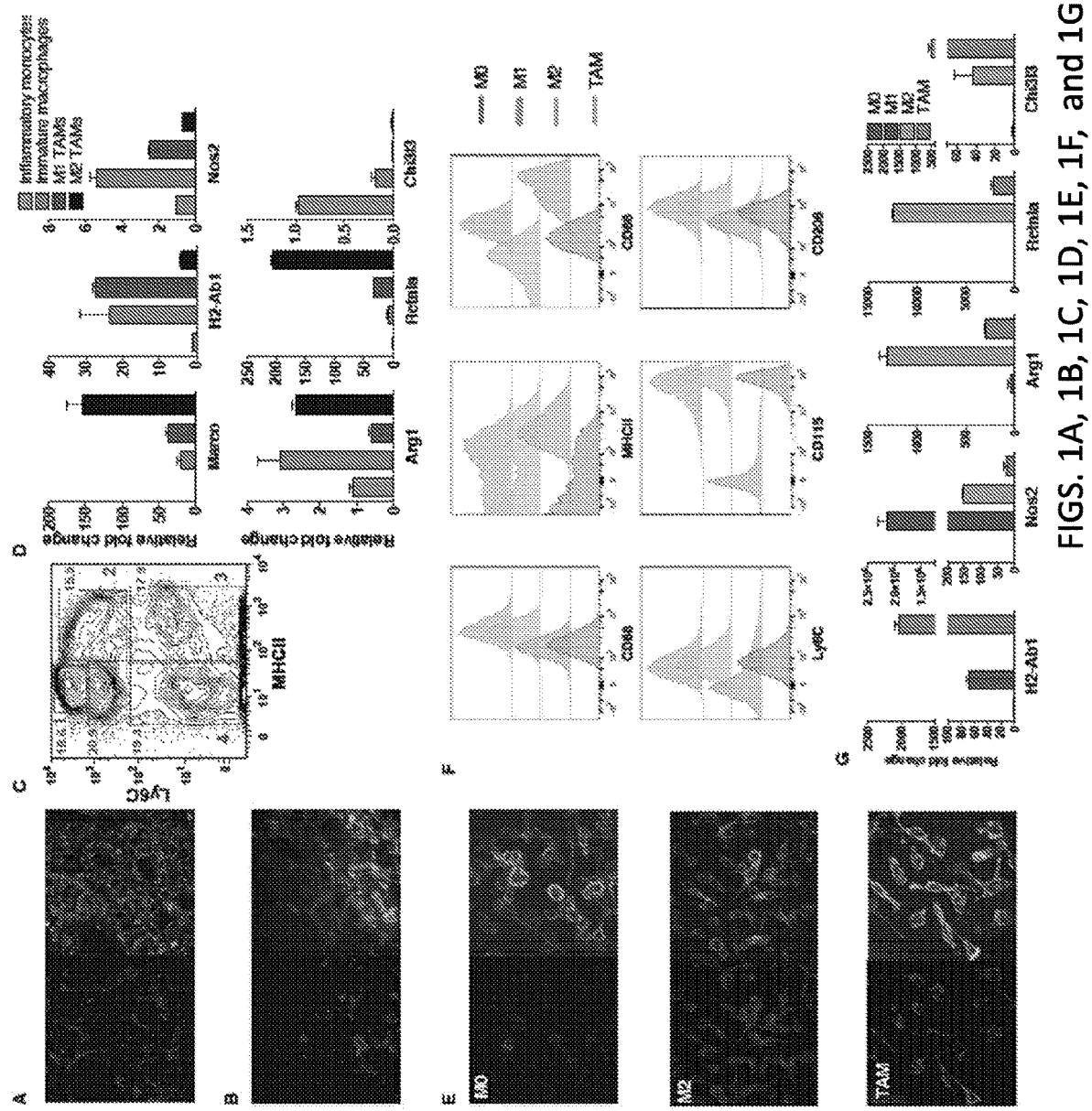
FIGS. 1A, 1B, 1C, 1D, 1E, 1F, and 1G

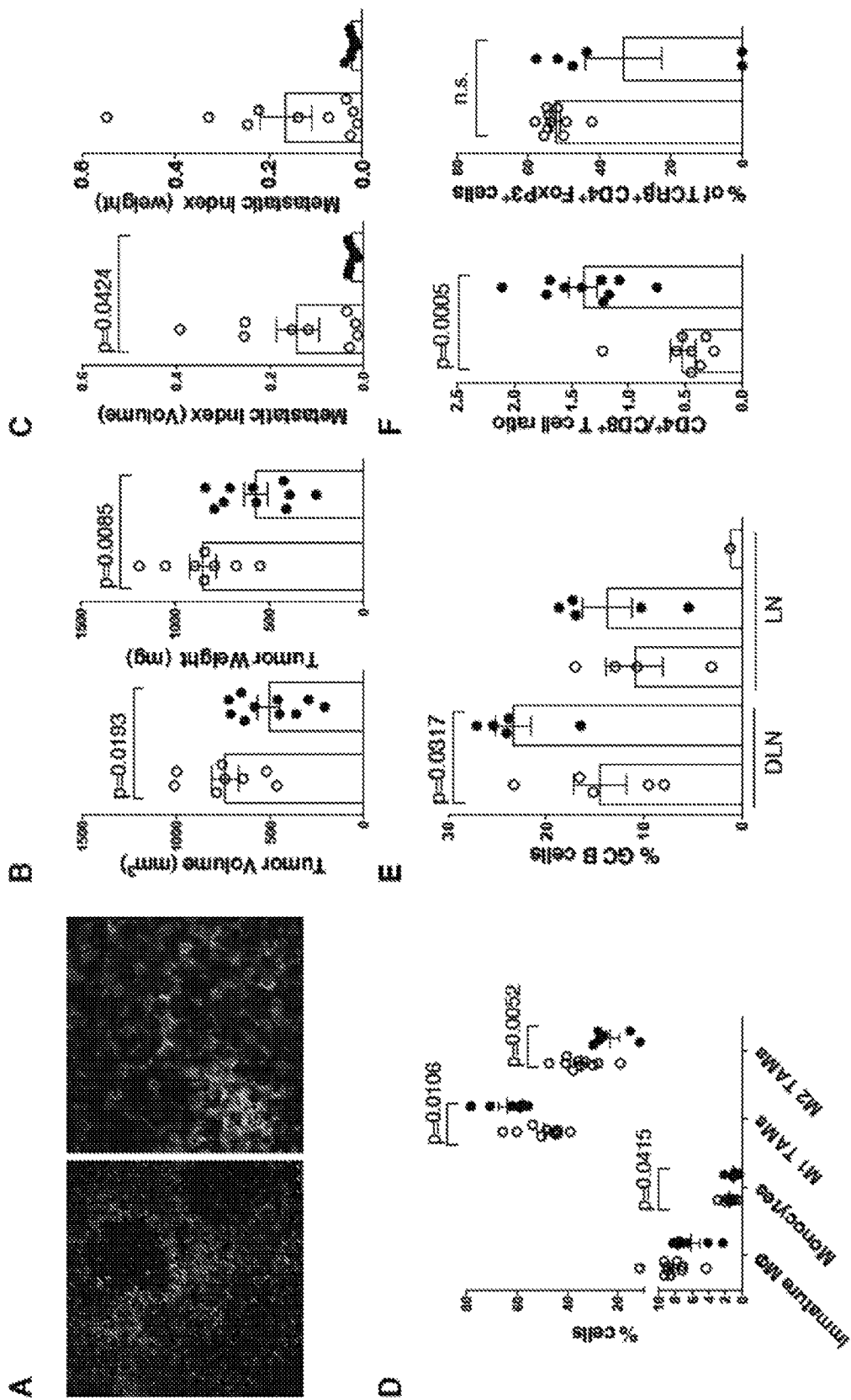
FIGS. 2A, 2B, 2C, 2D, 2E, and 2F

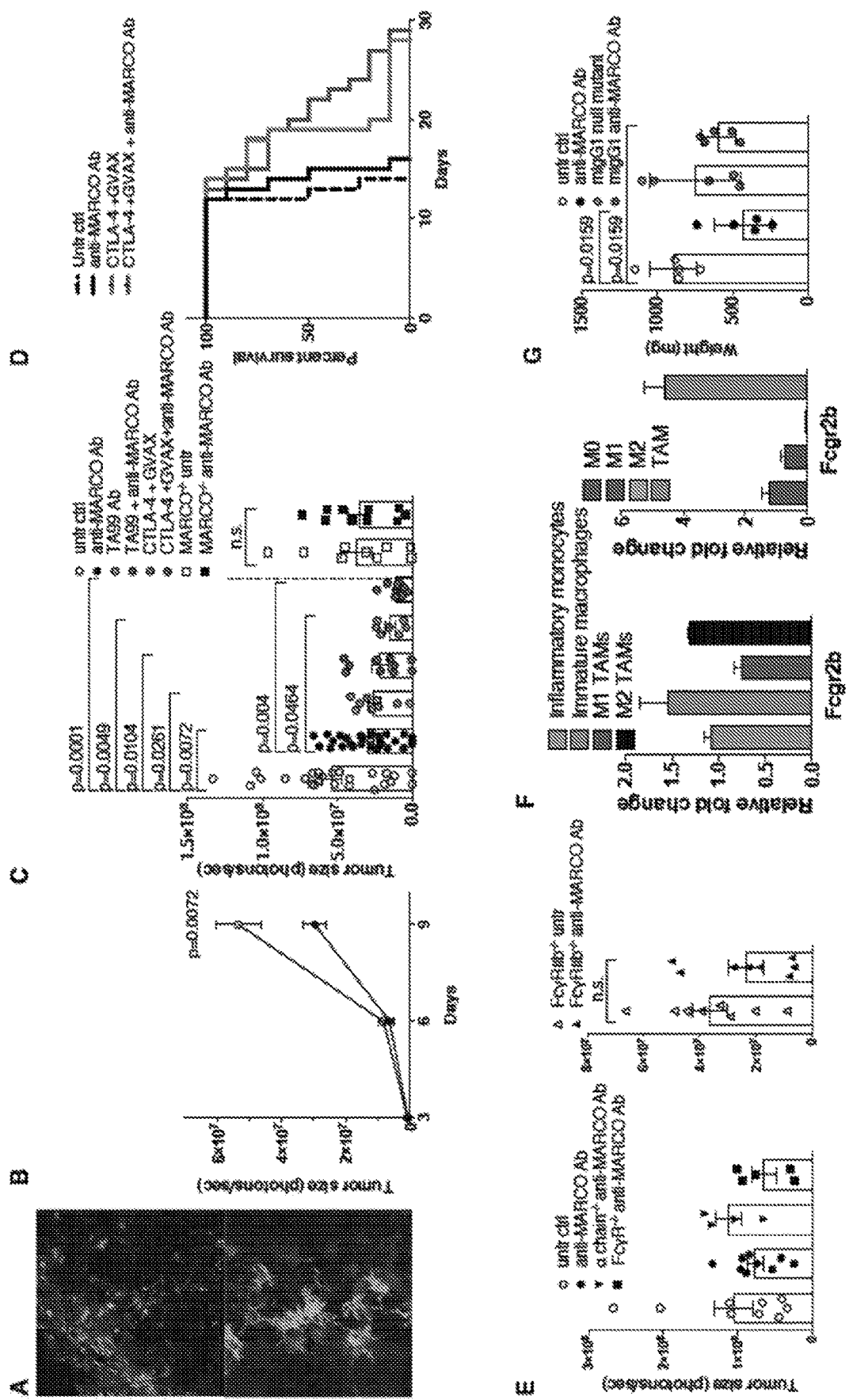
FIGS. 3A, 3B, 3C, 3D, 3E, 3F, and 3G

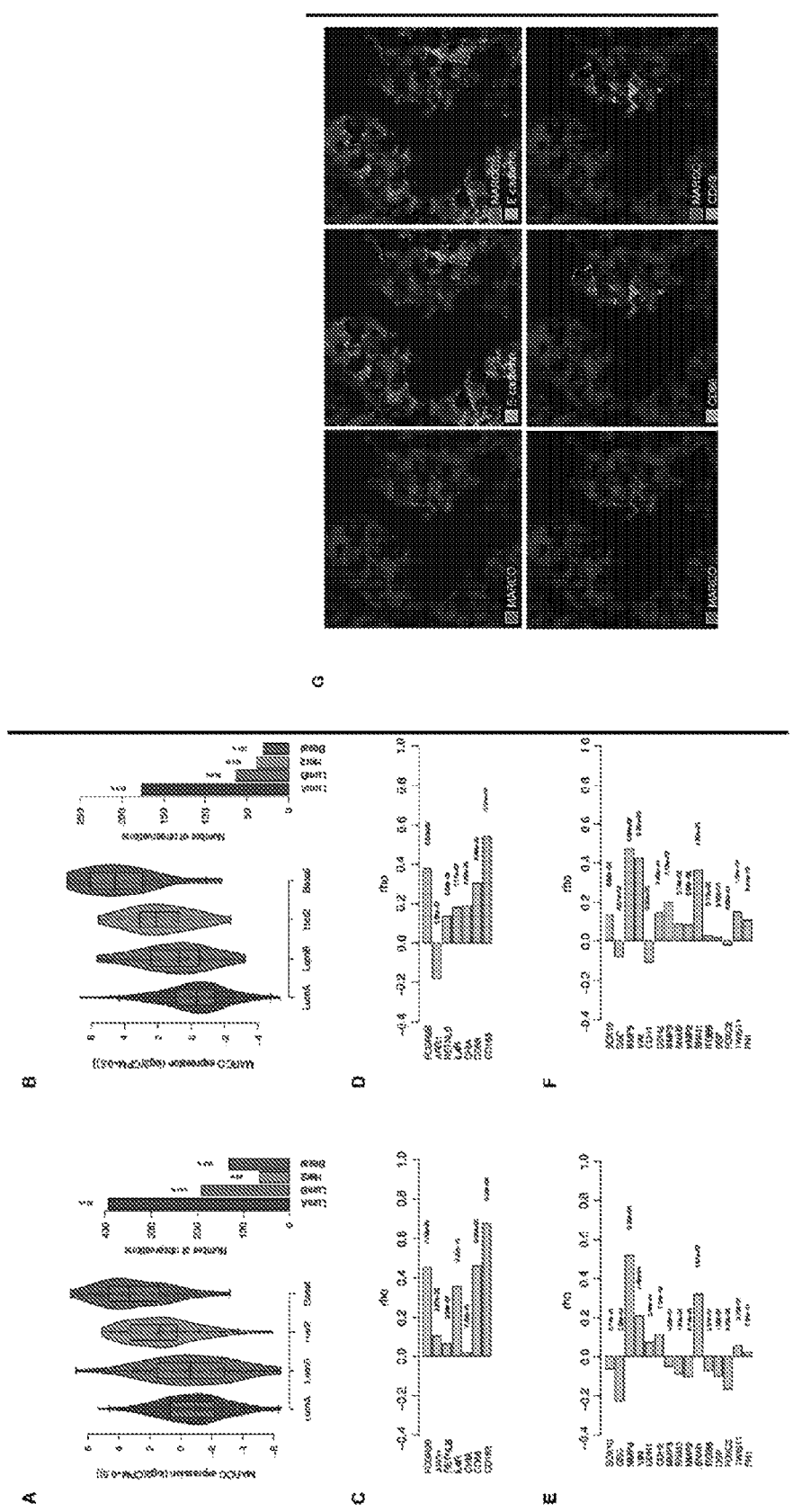
FIGS. 4A, 4B, 4C, 4D, 4E, 4F, and 4G

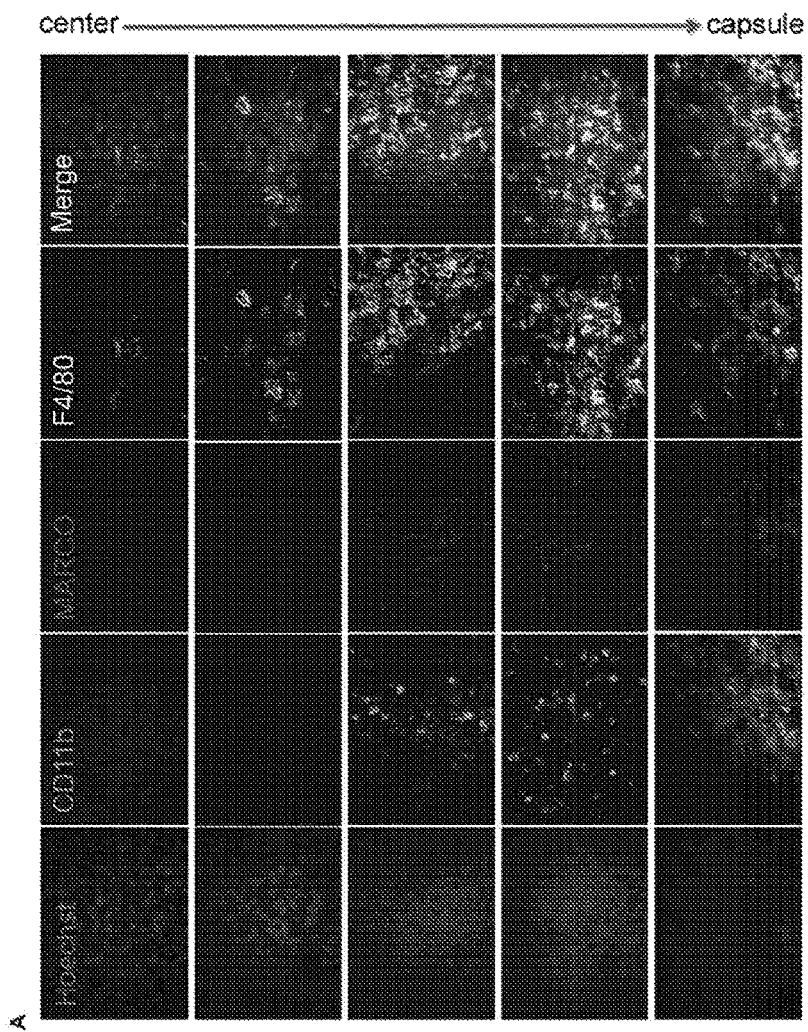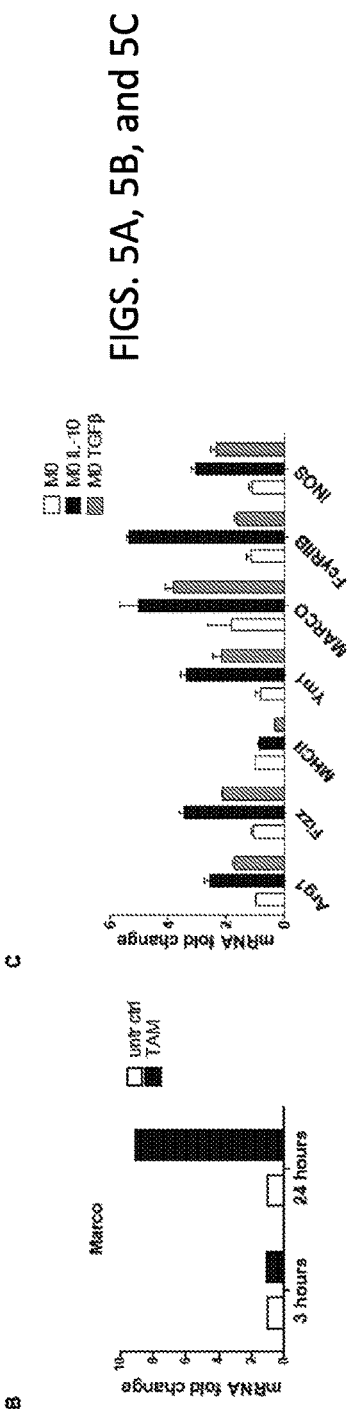
FIGS. 5A, 5B, and 5C

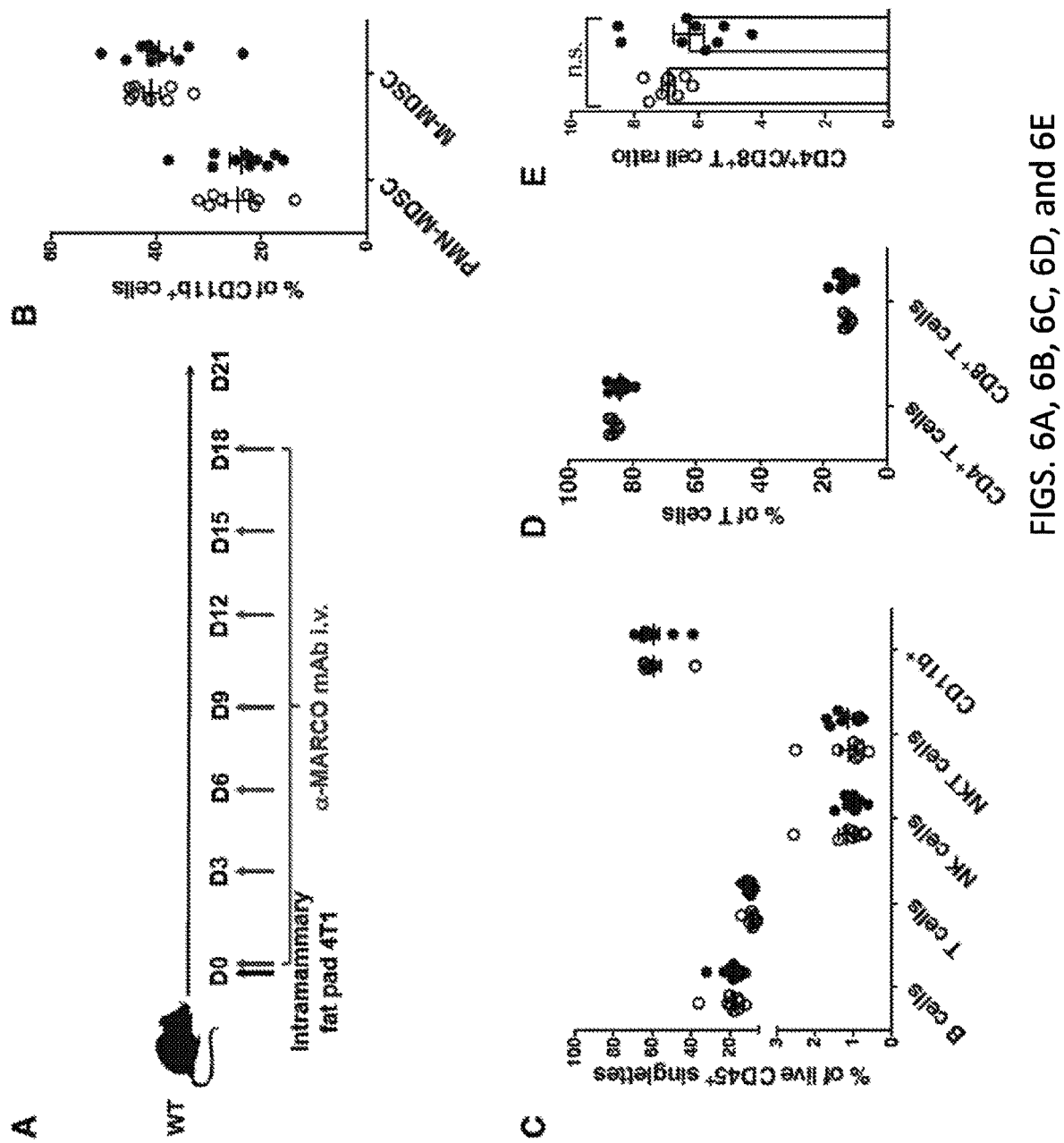
FIGS. 6A, 6B, 6C, 6D, and 6E

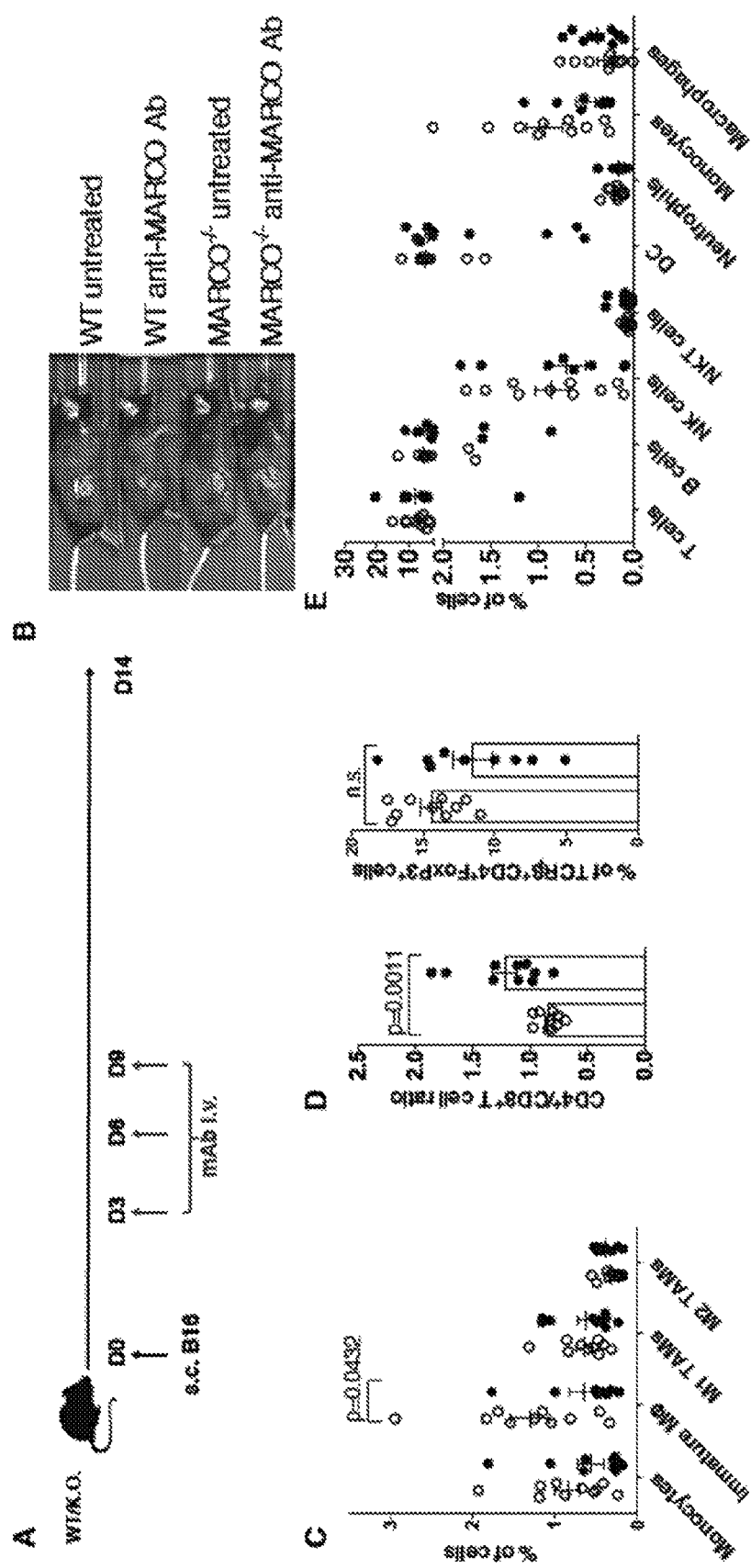
FIGS. 7A, 7B, 7C, 7D, and 7E

ANTI-TUMOR AGENTS AND METHODS OF USE

CROSS REFERENCE TO RELATED APPLICATIONS

This application claims priority to U.S. Provisional Application No. 62/169,920 filed on Jun. 2, 2015, and to U.S. Provisional Application No. 62/169,119 filed on Jun. 1, 2015. The content of the application is incorporated herein by reference in its entirety.

FIELD OF THE INVENTION

This invention relates to anti-tumor agents that target certain tumor-associated macrophages. The present invention further relates to methods of using such agents in treatment of cancer.

BACKGROUND OF THE INVENTION

Immunotherapy is now firmly established as an anti-tumor therapy, either alone or in conjunction with more traditional treatment options, including surgery and radiotherapy. The recent approvals of immune checkpoint therapies that enhance T cell-mediated immunity towards tumors offer potent ways to treat and even cure many types of cancer (1). The ability to manipulate the host anti-tumor T cell response has refocused efforts to target the immunosuppressive tumor microenvironment (TME) in ways that could synergize with T cell-targeted therapies.

However, the TME is a complex anatomical site in which most cell types of the immune system can be found. This includes lymphocytes such as T and B cells, and myeloid cells represented by different populations of macrophages such as tumor-associated macrophages (TAMs) and myeloid-derived suppressor cells (MDSCs) (2). TAMs differentiate from myeloid cells driven by cues from the growing tumor. As a reflection of the extreme plasticity of macrophages the phenotype and composition of TAMs vary between tumor types, a number of subpopulations existing with overlapping functions (3). In many cancers, the macrophage populations are dominated by immunosuppressive TAMs (4, 5). The TAMs support tumor progression by blocking anti-tumor immunity, and by secreting factors that promote angiogenesis and re-activation of epithelial-to-mesenchymal transition (EMT), which provides cancer cells with enhanced metastatic capabilities (6). A variety of macrophage markers have been investigated for selective expression on TAMs and have been evaluated for correlation with clinical outcome.

The Macrophage receptor with collagenous structure (MARCO) is a pattern recognition receptor of the Class A scavenger receptor family. It has a restricted expression pattern on subtypes of tissue resident macrophages in the lung, lymph nodes, spleen and peritoneum, but can also be upregulated by activated dendritic cells (7). Recently, MARCO was identified as a gene overexpressed in the TME and linked to poor prognosis in human breast cancer (8, 9). However, the role of MARCO in cancer progression is not known.

SUMMARY OF INVENTION

This invention relates to anti-tumor agents that target certain tumor-associated macrophages.

In one aspect, the invention provides an isolated antibody or an antigen-binding fragment thereof that specifically interacts and shows a measurable affinity to a macrophage receptor with collagenous structure (MARCO) epitope, further comprising (i) a variable light chain or (ii) a variable heavy chain of the antibody produced by an ED31 hybridoma.

In another aspect, the invention provides an isolated antibody or an antigen-binding fragment thereof that specifically interacts and shows a measurable affinity to a macrophage receptor with collagenous structure (MARCO) epitope comprising an amino acid sequence from SEQ ID NO: 1 further comprising (i) a variable light chain comprising CDRs1-3 of the light chain or (ii) a variable heavy chain comprising CDRs1-3 of the heavy chain of the antibody produced by an ED31 hybridoma.

In preferred embodiments, the above-described antibody or an antigen-binding fragment comprises an Fc region that binds to an inhibitory Fc-receptor, such as FcγRIIB The antibody can be a chimeric antibody, a humanized antibody, or humanized monoclonal antibody. The light or heavy chain of the isolated antibody or antigen-binding fragment differs from that of the antibody produced by the ED31 hybridoma.

The invention also provides a kit for detecting a macrophage receptor with collagenous structure (MARCO) epitope, comprising: (a) the antibody or a fragment antigen-binding thereof, capable of specifically binding in vitro to a macrophage receptor with collagenous structure (MARCO) epitope; and, (b) a reagent that binds, directly, or indirectly, to said antibody or the fragment thereof.

The invention further provides a method for quantifying the amount of a macrophage receptor with collagenous structure (MARCO) epitope in a tissue or fluid sample. The method comprises (a) obtaining the tissue or fluid sample from a subject; (b) contacting the tissue or fluid sample with an above-described antibody or fragment thereof that specifically binds to the macrophage receptor with collagenous structure (MARCO) epitope; and, (c) quantifying the amount of macrophage receptor with collagenous structure (MARCO) epitope in the sample.

In a further aspect, the invention provides a method of restricting tumor growth within a mammal in need thereof. The method comprises administering to the mammal a pharmaceutically effective amount of the above-described antibody or antigen-binding fragment thereof, which specifically interacts with the macrophage receptor with collagenous structure (MARCO) epitope so as to inhibit the tumor growth and metastatic spread. In this method, the mammal can be a human being suffering from cancer, such as breast cancer or a melanoma. The antibody can be a monoclonal antibody, a chimeric antibody, a humanized antibody, or humanized antibody. Preferably, the monoclonal antibody is a humanized monoclonal antibody or a human monoclonal antibody.

In yet another aspect, the invention provides a pharmaceutical composition comprising the isolated antibody or antigen-binding fragment thereof described above and a pharmaceutically acceptable carrier.

Another aspect of the invention features an isolated nucleic acid comprising a sequence encoding a chain of the isolated antibody or antigen-binding fragment describe above. The nucleic acid can be used to express a chain of the antibody or antigen-binding fragment of this invention or the antibody or fragment. For this purpose, one can operatively link the nucleic acid to suitable regulatory sequences to generate an expression vector. Accordingly, within the scope of this invention are a cultured host cell comprising the vector and a method for producing a polypeptide, the method comprising culturing the host cell under conditions in which the nucleic acid molecule is expressed.

The details of one or more embodiments of the invention are set forth in the description below. Other features, objectives, and advantages of the invention will be apparent from the description and from the claims.

BRIEF DESCRIPTION OF THE DRAWINGS

FIGS. 1A, 1B, 1C, 1D, 1E, 1F, and 1G are a set of photographs and diagrams showing identification of MARCO as a marker on M2 macrophages in tumor stroma of melanoma and mammary carcinoma. (FIG. 1A) Histological analysis of 4T1 mammary tumor. MARCO (red) is presented in an individual channel (left) and merged (right) including CD11b (green) and F4/80 (blue). (FIG. 1B) Histological analysis of B16 melanoma s.c tumor harvested on D10. MARCO (red) is presented in an individual channel (left) and merged (right) including DAPI (blue), CD11b (green) and F4/80 (magenta). (FIG. 1C) Flow cytometric analysis of macrophage subpopulations sorted from B16 tumors on D10. Pregated on live CD45$^+$CD11b$^+$ single cells; (1) Ly6C$^{hi}$ MHCII$^{lo}$ inflammatory monocytes, (2) Ly6C$^{int}$ MHCII$^{hi}$ Immature macrophages, (3) Ly6C$^{lo}$ MHCII$^{hi}$ M1 TAMs, (4) Ly6C$^{lo}$ MHCII$^{lo}$ M2 TAMs. (FIG. 1D) Relative expression of M1/M2 genes by qPCR on macrophage subpopulations 1-4 from FIG. 1C sorted from B16 tumors. (FIG. 1E) Histological analysis of polarized BMDMs. MARCO (red) is presented in an individual channel (left) and merged (right) including F4/80 (blue) and CD11b (green). (FIG. 1F) Flow cytometric analysis of surface marker expression on polarized BMDMs. (FIG. 1G) Relative expression of M1/M2 genes by qPCR on BMDMs. For (D) and (G) data show Mean±SEM with a C.I. of 95% of duplicates.

FIGS. 2A, 2B, 2C, 2D, 2E, and 2F are a set of photographs and diagrams showing that anti-MARCO mAb treatment inhibits tumor growth and metastasis by increasing the immunogenicity of the tumor microenvironment. (FIG. 2A) Histological analysis of 4T1 mammary tumors in which in vivo administered anti-MARCO mAb is detected in green on F4/80+ (blue) macrophages in 20× (left) and 63× (right). (FIG. 2B) 4T1 primary tumor volume (left) and weight (right) on D21. (FIG. 2C) Metastatic index based on volume (left) and weight (right) as measured by lung colony formation assay on D21. (FIG. 2D) Percentage of 4T1 tumor-infiltrating myeloid populations (1-4 from FIG. 1C) on D21. (FIG. 2E) Percentage of germinal center B cells in 4T1 tumor-draining vs non-draining inguinal lymph nodes in untreated controls and anti-MARCO mAb-treated mice on D21, and naïve inguinal lymph nodes. (FIG. 2F) 4T1 tumor-infiltrating CD4+/CD8+ T cell ratio on D21 (left). Frequencies of tumor-infiltrating T regulatory cells on D21 (right). Untreated control (○), anti-MARCO mAb (●), naïve non-tumor-bearing mouse (●). Data show Mean±SEM with a C.I. of 95% in 1 representative out of 3 independent experiments where n=10/group.

FIGS. 3A, 3B, 3C, 3D, 3E, 3F, and 3G are a photograph and a set of diagrams showing that anti-MARCO mAb treatment inhibits tumor growth through an FcR-dependent mechanism. (FIG. 3A) Histological analysis of B16 tumors. In vivo administered anti-MARCO mAb (green) detected on F4/80$^+$ (blue) macrophages, 63× (upper) and 100× (lower). (FIG. 3B) B16 tumor growth curves measured by IVIS on untreated and anti-MARCO mAb-treated mice. (FIG. 3C) Histograms representing B16 tumor size of different treatment groups on D9. Untreated control (○) and anti-MARCO mAb (●) treatment groups represent 4 independent experiments, n=25-30. For the remaining groups n=7-10. (FIG. 3D) Survival analysis of mice challenged with 0.1×10$^6$ B16luc tumor cells and vaccinated on days 3, 6, and 9 with 1×10$^6$ Gvax and the indicated antibody or combination i.v. Lack of survival was defined as tumor volume >1000 mm$^3$, n=10/group. (FIG. 3E) Histograms depicting B16 tumor size in FcR KO mouse strains compared to wildtype, n=4-9/group (left) and in FcγRIIb KO mice on D9, 2 independent experiments with n=4/group (right). (FIG. 3F) Relative expression of FcγRIIb in tumor-infiltrating myeloid populations (FIG. 1C, 1-4) compared to inflammatory monocytes (left) and BMDMs compared to M0 macrophages (right). Data show Mean±SEM with a C.I. of 95% of duplicates. (FIG. 3G) Histograms representing B16 tumor size of mice treated with Fc-modified anti-MARCO mAbs compared to untreated and ED31 treated mice on D10, n=5. Data show Mean±SEM with a C.I. of 95%. Survival curves were compared in groups of two and analyzed according to Mantel-Cox Log rank test; untr ctrl vs anti-MARCO Ab p=0.01; untr ctrl vs anti-CTLA-4 Ab p<0.0001; untr ctrl vs anti-CTLA-4 Ab+anti-MARCO Ab p=0.0002.

FIGS. 4A, 4B, 4C, 4D, 4E, 4F, and 4G are a set of photographs and diagrams showing that MARCO targets the tumor stroma of human basal mammary carcinoma. (FIG. 4A) Expression of MARCO (left panel) in human breast carcinoma subtypes and subtype distribution (right panel) in the TCGA dataset. (FIG. 4B) Expression of MARCO (left panel) in human breast carcinoma subtypes and subtype distribution (right panel) in the KI/Clinseq dataset. (FIG. 4C) Correlation of MARCO expression with M2 gene signature in the TCGA dataset. (FIG. 4D) Correlation of MARCO expression with M2 gene signature in the KI/Clinseq dataset. (FIG. 4E) Correlation of MARCO expression with EMT gene signature in the TCGA dataset. (FIG. 4F) Correlation of MARCO expression with EMT gene signature in the KI/Clinseq dataset. (FIG. 4G) Histological analysis of human basal breast carcinoma. Upper panel is stained for MARCO (red), EMT-marker E-cadherin (green) and DAPI (blue). Lower panel is stained for MARCO (red), macrophage marker CD68 (green) and DAPI (blue).

FIGS. 5A, 5B, and 5C are a set of photographs and diagrams showing characterization of MARCO expression on different macrophage populations. (FIG. 5A) Histological analysis of B16 tumors for DAPI (blue), CD11b (green), MARCO (red) and F4/80 (white), shown in individual channels and merged from the center to the periphery of the tumor. (FIG. 5B) Relative expression of MARCO by qPCR on IC-21 cells untreated (white) and treated with B16 tumor supernatant (black) after 3 and 24 hours, respectively. (FIG. 5C) Relative expression of M1/M2 genes by qPCR of BMDMs treated with IL-10 (black) and TGFβ (grey) for 24 hours, compared to untreated (white) M0. Data show Mean±SEM with a C.I. of 95% of duplicates.

FIGS. 6A, 6B, 6C, 6D, and 6E are a set of diagrams showing analysis of leukocyte infiltrate in the spleens of 4T1 tumor-bearing mice. (FIG. 6A) Schematic of the 4T1 mammary carcinoma model and mAb treatment regimen. Percentages of (FIG. 6B) polymorphonuclear and monocytic myeloid-derived suppressor cells within CD11b$^+$ cells of the spleen, (FIG. 6C) leukocyte subpopulations, (FIG. 6D) CD4$^+$ and CD8$^+$ T cells in the spleens of tumor-bearing mice. (FIG. 6E) depicts the splenic CD4$^+$/CD8$^+$ T cell ratio in tumor-bearing mice. Treatment groups are indicated as follows: untreated (○), anti-MARCO mAb treated (●) and naïve non-tumor-bearing (✼). Data show Mean±SEM with a C.I. of 95% in 1 representative out of 3 independent experiments where n=10/group.

FIGS. 7A, 7B, 7C, 7D, and 7E are a set of photographs and diagrams showing analysis of leukocyte infiltrate in the B16 tumors. (FIG. 7A) Schematic of the B16 melanoma tumor model and mAb treatment regimen. (FIG. 7B) Representative bioluminescence images of B16 tumors in WT and MARCO KO untreated or anti-MARCO mAb treated mice. (FIG. 7C) Percentage of B16 tumor-infiltrating myeloid populations (FIG. 1C, 1-4) on D10. (FIG. 7D) B16 tumor-infiltrating CD4$^+$/CD8$^+$ T cell ratio on D10. Frequencies of tumor-infiltrating T regulatory cells on D21 (right). Untreated control (○), anti-MARCO mAb (●). (FIG. 7E) Percentage of B16 tumor-infiltrating leukocyte populations on D10. (Treatment groups are indicated as follows: untreated (○), anti-MARCO mAb treated (●). Data show Mean±SEM with a C.I. of 95% in 1 representative out of at least 4 independent experiments where n=10/group.

DETAILED DESCRIPTION OF THE INVENTION

Tumor associated macrophages (TAMs) are a heterogeneous population of myeloid cells present in the tumor microenvironment (TME) of many solid tumors. TAMs are thought to contribute to immunosuppression enabling tumor establishment and progression into metastatic disease.

This invention is based, at least in part, on a number of unexpected discoveries. As disclosed herein, the pattern recognition scavenger receptor MARCO defines a subtype of TAMs and its expression is linked to poor clinical outcome in cancer, such as breast cancer. Shown below is the amino acid sequence of human MARCO (NCBI Reference Sequence: NP_006761.1).

(SEQ ID No: 1)

```
  1    mrnkkilked ellsetqqaa fhqiamepfe invpkpkrrn gvnfslavvv iylilltaga 61    gllvvqvlnl qarlrvlemy flndtlaaed spsfsllqsa hpgehlaqga srlqvlqaql 121    twvrvshehl lqrvdnftqn pgmfrikgeq gapglqghkg amgmpgapgp pgppaekgak 181    gamgrdgatg psgpqgppgv kgeaglqgpq gapgkqgatg tpgpqgekgs kgdggligpk 241    getgtkgekg dlglpgskgd rgmkgdagvm gppgaqgskg dfgrpgppgl agfpgakgdq 301    gqpglqgvpg ppgavghpga kgepgsagsp graglpgspg spgatglkgs kgdtglqgqq 361    grkgesgvpg pagvkgeqgs pglagpkgap gqagqkgdqg vkgssgeqgv kgekgergen 421    svsvrivgss nrgraevyys gtwgticdde wqnsdaivfc rmlgyskgra lykvgagtgq 481    iwldnvqcrg testlwsctk nswghhdcsh eedagvecsv
```

In particular, as shown in the examples below, an anti-MARCO monoclonal antibody induced anti-tumor activity in both breast carcinoma and melanoma models by reprogramming TAMs into a pro-inflammatory phenotype thereby rendering the tumor immunogenic. This anti-tumor activity is dependent on the ability of the Fc region of the anti-MARCO monoclonal antibody to engage the inhibitory Fc-receptor, FcγRIIB These demonstrate that immunotherapies using antibodies designed to modify myeloid cells of the TME represent a promising new mode of cancer treatment.

Antibodies

The present invention provides isolated antibodies, in particular monoclonal antibodies such as human monoclonal antibodies, that bind to MARCO and exhibit one or more desirable properties as disclosed herein. These properties include, for example, high affinity binding to human MARCO and low to intermediate affinity binding to inhibitory Fc-receptor, such as FcγRIIB Still further, antibodies of the invention have been shown to shift the anti-inflammatory, pro-tumorigenic and pro-metastatic TME to a more pro-inflammatory and less supportive TME for tumor progression.

Preferably the antibody is a human antibody, although the antibody can also be, for example, a murine antibody, a chimeric antibody or humanized antibody. In more preferred embodiments, the antibody binds to human MARCO with a $K_D$ of $5\times10^{-7}$ M or less, e.g., $1\times10^{-7}$ M, $5\times10^{-8}$ M, $1\times10^{-8}$ M, $5\times10^{-9}$ M, $1\times10^{-9}$ M or less, or binds to human MARCO with a $K_D$ of between $1\times10^{-8}$ M and $1\times10^{-10}$ M. Assays to evaluate the binding ability of the antibodies toward antigens are known in the art, including for example, ELISAs, Western blots and RIAs. The binding kinetics (e.g., binding affinity) of the antibodies also can be assessed by standard assays known in the art, such as by Biacore analysis.

In certain embodiments, the invention provides antibodies that comprise the heavy chain and light chain, or corresponding CDR1s, CDR2s and CDR3s of antibodies derived from the ED31 hybridoma. The CDR regions are delineated using the Kabat system (Kabat, E. A., et al. (1991) Sequences of Proteins of Immunological Interest, Fifth Edition, U.S. Department of Health and Human Services, NIH Publication No. 91-3242). Listed below are nucleic acid sequences encoding the rat anti-mouse MARCO (ED31) heavy and light chain and corresponding amino acid sequences, where the corresponding CDR regions are in bold, i.e., GYTFTDYW, ISPNSGTT, and TRCRYTTGVHYFDY for heavy CDRs 1-3 (SEQ ID Nos: 30-32, respectively) and SQSLLDSDGNSY, LVS, and MQATHAPWT for light chain CDRs 1-3 (SEQ ID Nos: 33-35, respectively).

Heavy chain:

(SEQ ID No: 2)

GGGGGGGGGGGATAAGATCACTGTCCTCTCTACAGTCACTGAGTACAAA

GGACCTCACCATGGGATG

GATCTGTATCATCTTTCTTGTGGCAACAGCTACAGGTGTCCTCCCCCAGG

TCAAGCTGCTGCAGTCTGG

GGCTGCATTGGTGAAGCCTGGAGCCTCTGTGAAGATGTCTTGCAAAGCTT

```
CTGGTTATACATTCACTGAC

TACTGGGTGAGCTGGGTGAAGCAGAGTCATGGAAAGAGCCTTGAGTGCAT

TGGGGAAATTTCTCCTAACA

GTGGTACTACTAACTTCAATGAAAAGTTCAAGGGCAAGGCCACATTGACT

GTAGACAAATCCACCAGCAC

AGCCTATATGGAGCTCAGCAGATTGACATCTGAGGACTCTGCAATCTATT

ACTGTACAAGATGCAGGTAT

ACTACCGGAGTCCATTACTTTGATTACTGGGGCCAAGGAGTCATGGTCAC

AGTCTCCTCAGCTGAAACAA

CAGCCCCATCTGTCTATCCACTGGCTCCTGGAACTGCTCTCAAAAGTAAC

TCCATGGTGACCCTGGGATG

CCTGGT

CAAGGGCTATTTCCCTGAGCCAGTCACCGTGACCTGGAACTCTGGAGCCC

TGTCCAGCGGTGTGCACACCTTCCCAGCTGTCCTGCAGTCTGGGCTCTAC

ACTCTCACCAGCTCAGTGACTGTACCCTCCA

GCACCTGGCCCAGCCAGACCGTCACCTGCAACGTAGCCCACCCGGCCAGC

AGCACCAAGGTGGACAAG

AAAATTGAGAAGGGCGAATTCGCAACCTACATGGCCGCC (SEQ ID No: 3)
GGGGIRSLSSLQSLSTKDLTMGWICIIFLVATATGVLPQVKLLQSGAALV

KPGASVKMSCKASGYTFTDYWVSWVKQSHGKSLECIGEISPNSGTTNFNE

KFKGKATLTVDKSTSTAYMELSRLTSEDSAIYYCTRCRYTTGVHYFDYWG

QGVMVTVSSAETTAPSVYPLAPGTALKSNSMVTLGCLVKGYFPEPVTVTW

NSGALSSGVHTFPAVLQSGLYTLTSSVTVPSSTWPSQTVTCNVAHPASST

KVDKKIEKGEFATYMAA

Light chain:
                                           (SEQ ID No: 4)
GGGGGGGGGGGGGTGATTCCACTTCTAATTTCATCTCCTCAA

AACGATGAGTCCTGCCAGTCCCTGTTTTTATTATTGCTTTGGATTCTGGG

AACCAAAGGTGATGTTGTGCTGACCCAGACTCCATCCATATTGTCTGTTA

CCATTGGACAATCGGTCTCCATCTCTTGC

AGGTCAAGTCAGAGTCTCTTAGATAGTGATGGAAACAGCTATTTATATTG

GTTCCTACAGAGGCCAGGCCAGTCTCCACAGCGTCTAATTTATTTGGTAT

CCAATTTGGGATCTGGGGTCCCCAACAG

GTTCAGTGGCAGTGGGTCAGGAACAGATTTCACACTCAAAATCAGTGGAG

TGGAGGCTGAGGATTTGGGAGT

TTATTACTGCATGCAAGCTACCCATGCTCCGTGGACGTTCGGTGGAGGCA

CCAAGCTGGAATTGAAACGGGC

TGATGCTGCACCAACTGTATCTATCTTCCCACCATCCACGGAACAGTTAG

CAACTGGAGGTGCCTCAGTCGT

GTGCCTCATGAACAACTTCTATCCCAGAGACATCAGTGTCAAGTGGAAGA

TTGATGGCACTGAACGACGAGA

TGGTGTCCTGGACAGTGTTACTGATCAGGACAGCAAAGACAGCACGTACA

GCATGAGCAGCACCCTCTCGT

TGACCAAGGCTGACTATGAAAGTCATAACCTCTATACCTGTGAGGTTGTT

CATAAACATCATCCTCAC

CCAGGGCGAATTCCAGCAACTGGCGCTTACTAGGGCCGACCGCCAG (SEQ ID No: 5)
GGGGVIPLLISSPQNDESCQSLFLLLLWILGTKGDVVLTQTPSILSVTIG

QSVSISCRSSQSLLDSDGNSYLYWFLQRPGQSPQRLIYLVSNLGSGVPNR

FSGSGSGTDFTLKISGVEAEDLGVYYCMQATHAPWTEGGGIKLELKRADA

APTVSIFPPSTEQLATGGASVVCLMNNEYPRDISVKWKIDGTERRDGVLD

SVTDQDSKDSTYSMSSTLSLTKADYESHNLYTCEVVHKHHPHPGRIPATG

AY
```

Shown below are nucleic acid sequences and amino acid sequences for heavy chain and light chain variable regions, where the corresponding CDR regions are in bold, i.e., GYTFTDYW, ISPNSGTT, and TRCRYTTGVHYFDY for heavy CDRs 1-3 (SEQ ID Nos: 30-32, respectively) and SQSLLDSDGNSY, LVS, and MQATHAPWT for light chain CDRs 1-3 (SEQ ID Nos: 33-35, respectively).

```
ED31 variable heavy chain (starts with EcoRI site,
end with XhoI site)
                                          (SEQ ID No: 24)
GAATTCCACCATGGGATGGATCTGTATCATCTTTCTTGTGGCAACAGCTA

CAGGTGTCCTCTCCCAGGTCAAGCTGCTGCAGTCTGGGGCTGCATTGGTG

AAGCCTGGAGCCTCTGTGAAGATGTCTTGCAAAGCTTCTGGTTATACATT

CACTGACTACTGGGTGAGCTGGGTGAAGCAGAGTCATGGAAAGAGCCTTG

AGTGCATTGGGGAAATTTCTCCTAACAGTGGTACTACTAACTTCAATGAA

AAGTTCAAGGGCAAGGCCACATTGACTGTAGACAAATCCACCAGCACAGC

CTATATGGAGCTCAGCAGATTGACATCTGAGGACTCTGCAATCTATTACT

GTACAAGATGCAGGTATACTACCGGAGTCCATTACTTTGATTACTGGGGC

CAAGGAGTCATGGTCACAGTCTCGAGC
                                          (SEQ ID No: 25)
NSTMGWICIIFLVATATGVLSQVKLLQSSGAALVKPGASVKMSCKASGYT
FTDYWVSWVKQSHGKSLECIGEISPNSGTTNFNEKFKGKATLTVDKSTST
AYMELSRLTSEDSAIYYCTRCRYTTGVHYFDYWGQGVMVTVSS

ED31 human variable light chain kappa (starts with
EcoRI site)
                                          (SEQ ID No: 26)
GAATTCCACCATGAGTCCTGTCCAGtCCCTGTTTTTATTATTGCTTTGGA

TTCTGGGAACCAAAGGTGATGTTGTGCTGACCCAGACTCCATCCATATTG

TCTGTTACCATTGGACAATCGGTCTCCATCTCTTGCAGGTCAAGTCAGAG

TCTCTTAGATAGTGATGGAAACAGCTATTTATATTGGTTCCTACAGAGGC

CAGGCCAGTCTCCACAGCGTCTAATTTATTTGGTATCCAATTTGGGATCT

CGGGGTCCCCAACAGGTTCAGTGGCAGTGGGTCAGGAACAGATTTCACAC

TAAAATCAGTGGAGTGGAGGCTGAGGATTTGGGAGTTTATTACTGCATGC

AAGCTACCCATGCTCCGTGGACGTTCGGTGGAGGCACCAAGCTGGAATTG

AAACGA
```

-continued (SEQ ID No: 27)
NSTMSPVQSLFLLLLWILGTKGDVVLTQTPSILSVTIGQSVSISCRS**SQS
LLDSDGNSYLYWFLQRPGQSPQRLIYLVS**NLGSGVPNRFSGSGSGTDFTL
KISGVEAEDLGVYYCMQATHAPWTFGGGTKLELKR ED31 mouse variable light chain kappa (starts with
EcoRI site)
(SEQ ID No: 28)
GAATTCCACCATGAGTCCTGTCCAGTCCCTGTTTTTATTATTGCTTTGGA

TTCTGGGAACCAAAGGTGATGTTGTGCTGACCCAGACTCCATCCATATTG

TCTGTTACCATTGGACAATCGGTCTCCATCTCTTGCAGGTCAAGTCAGAG

TCTCTTAGATAGTGATGGAAACAGCTATTTATATTGGTTCCTACAGAGGC

CAGGCCAGTCTCCACAGCGTCTAATTTATTTGGTATCCAATTTGGGATCT

GGGGTCCCCAACAGGTTCAGTGGCAGTGGGTCAGGAACAGATTTCACACT

CAAAATCAGTGGAGTGGAGGCTGAgGATTTGGGAGTTTATTACTGCATGC

AAGCTACCCATGCTCCGTGGACGTTCGGTGGAGGCACCAAGCTGGAATTG

AAACG (SEQ ID No: 29)
NSTMSPVQSLFLLLLWILGTKGDVVLTQTPSILSVTIGQSVSISCRS**SQS
LLDSDGNSYLYWFLQRPGQSPQRLIYLVS**NLGSGVPNRFSGSGSGTDFTL
KISGVEAEDLGVYYCMQATHAPWTFGGGTKLELKR

In other embodiments, the $V_H$ and/or $V_L$ amino acid sequences of the antibodies may be 85%, 90%, 95%, 96%, 97%, 98% or 99% homologous to the sequences set forth above. An antibody having $V_H$ and $V_L$ regions having high (i.e., 80% or greater) homology to the $V_H$ and $V_L$ regions of the sequences set forth above, can be obtained by mutagenesis (e.g., site-directed or PCR-mediated mutagenesis) of nucleic acid molecules encoding the above-mentioned heavy chain and light chain, or related CDR1s, CDR2s and CDR3s, followed by testing of the encoded altered antibody for retained function using the functional assays described herein. Shown in FIGS. 8 and 9 are sequences encoding a number of $V_H$ or $V_L$ variants as well as corresponding consensus sequences. Among them, the H03 and L06 were selected and further evaluated as discussed in the examples below.

As used herein, the percent homology between two amino acid sequences is equivalent to the percent identity between the two sequences. The percent identity between the two sequences is a function of the number of identical positions shared by the sequences (i.e., % homology=# of identical positions/total # of positions ×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two amino acid sequences can be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. 48:444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6.

Additionally or alternatively, the protein sequences of the present invention can further be used as a "query sequence" to perform a search against public databases to, for example, identify related sequences. Such searches can be performed using the XBLAST program (version 2.0) of Altschul, et al. (1990) J. Mol. Biol. 215:403-10. BLAST protein searches can be performed with the XBLAST program, score=50, wordlength=3 to obtain amino acid sequences homologous to the antibody molecules of the invention. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and NBLAST) can be used. (See www.ncbi.nlm.nih.gov).

Antibodies with Conservative Modifications

In certain embodiments, an antibody of the invention comprises a heavy chain variable region comprising CDR1, CDR2 and CDR3 sequences and a light chain variable region comprising CDR1, CDR2 and CDR3 sequences, wherein one or more of these CDR sequences comprise specified amino acid sequences based on the preferred antibodies described herein, or conservative modifications thereof, and wherein the antibodies retain the desired functional properties of the anti-MARCO antibodies of the invention.

As used herein, the term "conservative sequence modifications" refers to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine).

Thus, one or more amino acid residues within the CDR regions of an antibody of the invention can be replaced with other amino acid residues from the same side chain family and the altered antibody can be tested for retained function using the functional assays described herein.

In another embodiment, the invention provides antibodies that bind to the same epitope on human MARCO as any of the anti-MARCO monoclonal antibodies of the invention (i.e., antibodies that have the ability to cross-compete for binding to MARCO with any of the monoclonal antibodies of the invention). Such cross-competing antibodies can be identified based on their ability to cross-compete with an antibody disclosed herein in standard MARCO binding assays. For example, BIAcore analysis, ELISA assays or flow cytometry may be used to demonstrate cross-competition with the antibodies of the current invention.

An antibody of the invention further can be prepared using an antibody having one or more of the $V_H$ and/or $V_L$ sequences disclosed herein as starting material to engineer a modified antibody, which modified antibody may have altered properties from the starting antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain CDRs. For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) Nature 332:323-327; Jones, P. et al. (1986) Nature 321:522-525; Queen, C. et al. (1989) Proc. Natl. Acad. See. U.S.A. 86:10029-10033; U.S. Pat. No. 5,225,539 to Winter, and U.S. Pat. Nos. 5,530,101; 5,585,089; 5,693,762 and 6,180,370 to Queen et al.)

Such framework sequences can be obtained from public DNA databases or published references that include germline antibody gene sequences. For example, germline DNA sequences for human heavy and light chain variable region genes can be found in the "VBase" human germline sequence database (available at www.mrc-cpe.cam.ac.uk/vbase), as well as in Kabat, E. A., et al. (1991) Sequences of Proteins of Immunological Interest, Fifth Edition, U.S. Department of Health and Human Services, NIH Publication No. 91-3242; Tomlinson, I. M., et al. (1992) "The Repertoire of Human Germline $V_H$ Sequences Reveals about Fifty Groups of $V_H$ Segments with Different Hypervariable Loops" J. Mol. Biol. 227:776-798; and Cox, J. P. L. et al. (1994) "A Directory of Human Germ-line $V_H$ Segments Reveals a Strong Bias in their Usage" Eur. J. Immunol. 24:827-836; the contents of each of which are incorporated herein by reference.

As another example, the germline DNA sequences for human heavy and light chain variable region genes can be found in the GenBank database. For example, the following heavy chain germline sequences found in the HCo7 HuMAb mouse are available in the accompanying GenBank accession numbers: 1-69 (NG_0010109, NT_024637 and BC070333), 3-33 (NG_0010109 and NT_024637) and 3-7 (NG_0010109 and NT_024637). As another example, the following heavy chain germline sequences found in the HCo12 HuMAb mouse are available in the accompanying GenBank accession numbers: 1-69 (NG_0010109, NT_024637 and BC070333), 5-51 (NG_0010109 and NT_024637), 4-34 (NG_0010109 and NT_024637), 3-30.3 (AJ556644) and 3-23 (AJ406678).

The $V_H$ CDR1, CDR2, and CDR3 sequences, and the $V_K$ CDR1, CDR2, and CDR3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370).

Another type of variable region modification is to mutate amino acid residues within the $V_H$ and/or $V_K$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Preferably conservative modifications (as discussed above) are introduced. The mutations may be amino acid substitutions, additions or deletions, but are preferably substitutions. Moreover, typically no more than one, two, three, four or five residues within a CDR region are altered.

Engineered antibodies of the invention include those in which modifications have been made to framework residues within $V_H$ and/or $V_K$, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter its glycosylation, again to alter one or more functional properties of the antibody. The numbering of residues in the Fc region is that of the EU index of Kabat.

In still another embodiment, the glycosylation of an antibody can be modified. Glycosylation can be altered to, for example, increase or decrease the affinity of the antibody for antigen or an Fc receptor. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such an approach is described in further detail in U.S. Pat. Nos. 8,008,449 and 6,350,861. In preferred embodiments, the antibody has a higher affinity to FcγIIB than an unmodified IgG Fc.

Another modification of the antibodies herein is pegylation. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. Methods for pegylating proteins are known in the art and can be applied to the antibodies of the invention. See for example, EP 0 154 316 by Nishimura et al. and EP 0 401 384 by Ishikawa et al.

Nucleic Acid Molecules

Another aspect of the invention provides nucleic acid molecules that encode the antibodies or chains thereof of the invention. The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. (1987) Current Protocols in Molecular Biology, Greene Publishing and Wiley Interscience, New York. A nucleic acid of the invention can be, for example, DNA or RNA and may or may not contain intronic sequences. In a preferred embodiment, the nucleic acid is a cDNA molecule.

Nucleic acids of the invention can be obtained using standard molecular biology techniques. For antibodies expressed by hybridomas (e.g., hybridomas prepared from transgenic mice carrying human immunoglobulin genes), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

Once DNA fragments encoding $V_H$ and $V_L$ segments are obtained, these DNA fragments can be further manipulated by standard recombinant DNA techniques, for example to convert the variable region genes to full-length antibody chain genes, to Fab fragment genes or to a scFv gene. In these manipulations, a $V_H$- and $V_L$-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the $V_H$-encoding DNA to another DNA molecule encoding heavy chain constant regions (CH1, CH2 and CH3). The sequences of human heavy chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region. For a Fab fragment heavy chain gene, the $V_H$-encoding DNA can be operatively linked to another DNA molecule encoding only the heavy chain CH1 constant region.

The isolated DNA encoding the $V_L$ region can be converted to a full-length light chain gene (as well as a Fab light chain gene) by operatively linking the $V_L$-encoding DNA to another DNA molecule encoding the light chain constant region, CL. The sequences of human light chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region, but preferably is a kappa constant region.

To create a scFv gene, the $V_H$- and $V_L$-encoding DNA fragments are operatively linked to another fragment encoding a flexible linker, e.g., encoding the amino acid sequence $(Gly_4-Ser)_3$, such that the $V_H$- and $V_L$ sequences can be expressed as a contiguous single-chain protein, with the $V_H$ and $V_L$ regions joined by the flexible linker (see e.g., Bird et al. (1988) Science 242:423-426; Huston et al. (1988) Proc. Natl. Acad. Sci. USA 85:5879-5883; McCafferty et al., (1990) Nature 348:552-554).

Production of Monoclonal Antibodies

Monoclonal antibodies (mAbs) of the invention can be produced by a variety of techniques, including conventional monoclonal antibody methodology e.g., the standard somatic cell hybridization technique of Kohler and Milstein (1975) Nature 256: 495. Although somatic cell hybridization procedures are preferred, in principle, other techniques for producing monoclonal antibody can be employed e.g., viral or oncogenic transformation of B lymphocytes.

The preferred animal system for preparing hybridomas is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known.

Chimeric or humanized antibodies of the present invention can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567). To create a humanized antibody, the murine CDR regions can be inserted into a human framework using methods known in the art (see e.g. U.S. Pat. Nos. 5,225,539, 5,530, 101, 5,585,089, 5,693,762, and 6,180,370).

In a preferred embodiment, the antibodies of the invention are human monoclonal antibodies. Such human monoclonal antibodies directed against MARCO can be generated using transgenic or transchromosomic mice carrying parts of the human immune system rather than the mouse system. These transgenic and transchromosomic mice include mice referred to herein as HuMAb mice and KM Mice™, respectively, and are collectively referred to herein as "human Ig mice." See e.g., Lonberg, et al. (1994) Nature 368(6474): 856-859) reviewed in Lonberg, N. (1994) Handbook of Experimental Pharmacology 113:49-101; Lonberg, N. and Huszar, D. (1995) Intern. Rev. Immunol. 13: 65-93, and Harding, F. and Lonberg, N. (1995) Ann. N.Y. Acad. Sci. 764:536-546). The preparation and use of HuMab mice, and the genomic modifications carried by such mice, is further described in Taylor, L. et al. (1992) Nucleic Acids Research 20:6287-6295; Chen, J. et al. (1993) International Immunology 5: 647-656; Tuaillon et al. (1993) Proc. Natl. Acad. Sci. USA 90:3720-3724; Choi et al. (1993) Nature Genetics 4:117-123; Chen, J. et al. (1993) EMBO J. 12: 821-830; Tuaillon et al. (1994) J. Immunol. 152:2912-2920; Taylor, L. et al. (1994) International Immunology 6: 579-591; and Fishwild, D. et al. (1996) Nature Biotechnology 14: 845-851, the contents of all of which are hereby specifically incorporated by reference in their entirety. See also U.S. Pat. Nos. 8,008,449, 5,545,806, 5,569,825, 5,625,126, 5,633,425, 5,789,650, 5,877,397, 5,661,016, 5,814,318, 5,874,299, 5,770,429, and 5,545,807; WO 92/03918, WO 93/12227, WO 94/25585, WO 97/13852, WO 98/24884, WO 99/45962, WO 01/144, and WO 02/43478.

Still further, alternative transgenic animal systems expressing human immunoglobulin genes are available in the art and can be used to raise anti-MARCO antibodies of the invention. For example, an alternative transgenic system referred to as the XENOMOUSE (ABGENIX, INC.) can be used; such mice are described in, for example, U.S. Pat. Nos. 5,939,598, 6,075,181, 6,114,598, 6,150,584, and 6,162,963. Moreover, alternative transchromosomic animal systems expressing human immunoglobulin genes are available in the art and can be used to raise anti-MARCO antibodies of the invention. For example, mice carrying both a human heavy chain transchromosome and a human light chain transchromosome, referred to as "TC mice" can be used; such mice are described in Tomizuka et al. (2000) Proc. Natl. Acad. Sci. USA 97:722-727. Another example is the Velocimmune mouse from Regeneron (Proc Natl Acad Sci USA. 2014 Apr. 8; 111(14):5153-8). Furthermore, cows carrying human heavy and light chain transchromosomes have been described in the art (Kuroiwa et al. (2002) Nature Biotechnology 20:889-894) and can be used to raise anti-MARCO antibodies of the invention.

Human monoclonal antibodies of the invention can also be prepared using phage display methods for screening libraries of human immunoglobulin genes. Such phage display methods for isolating human antibodies are established in the art. See for example: U.S. Pat. Nos. 5,223,409, 5,403,484, 5,571,698, 5,427,908, 5,580,717, 5,969,108, 6,172,197, 5,885,793, 6,521,404, 6,544,731, 6,555,313, 6,582,915, and 6,593,081.

Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767.

Antibodies of the invention also can be produced in a host cell using, for example, a combination of recombinant DNA techniques and gene transfection methods as is well known in the art (e.g., Morrison, S. (1985) Science 229:1202).

For example, to express the antibodies, or antibody fragments thereof, DNAs encoding partial or full-length light and heavy chains, can be obtained by standard molecular biology techniques (e.g., PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes can be inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the Vk segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. Methods in Enzymology 185, Academic Press, San Diego, Calif. (1990)). It will be appreciated by those skilled in the art that the design of the expression vector, including the selection of regulatory sequences, may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP) and polyoma. Alternatively, nonviral regulatory sequences may be used, such as the ubiquitin promoter or β-globin promoter. Still further, regulatory elements composed of sequences from different sources, such as the SRα promoter system, which contains sequences from the SV40 early promoter and the long terminal repeat of human T cell leukemia virus type 1 (Takebe, Y. et al. (1988) Mol. Cell. Biol. 8:466-472).

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665, and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains can be transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody.

Preferred mammalian host cells for expressing the recombinant antibodies of the invention include Chinese Hamster Ovary (CHO cells) (including dhfr-CHO cells, described in Urlaub and Chasin, (1980) Proc. Natl. Acad. Sci. USA 77:4216-4220, used with a DHFR selectable marker, e.g., as described in R. J. Kaufman and P. A. Sharp (1982) Mol. Biol. 159:601-621), NSO myeloma cells, COS cells and SP2 cells. In particular, for use with NSO myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Pharmaceutical Compositions

The present invention also provides a composition, e.g., a pharmaceutical composition, containing one or a combination of monoclonal antibodies, or antigen-binding portion(s) thereof, of the present invention, formulated together with a pharmaceutically acceptable carrier. Such compositions may include one or a combination of (e.g., two or more different) antibodies of the invention. For example, a pharmaceutical composition of the invention can comprise a combination of antibodies that bind to different epitopes on the target MARCO antigen.

Therapeutic formulations of the antibody can be prepared by mixing the antibody having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN, PLURONICS, or polyethylene glycol (PEG).

The formulation may also contain more than one active compound as necessary for the particular indication being treated, preferably those with complementary activities that do not adversely affect each other. For instance, the formulation may further comprise another antibody, cytotoxic agent, or a chemotherapeutic agent. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g., films, or microcapsule. Examples of sustained-releasable matrices include polyesters, hydrogels (for example, poly(2-hydroxyethyl-methacrylate), or poly(vinyl-alcohol)), polylactides (U.S. Pat. No. 3,773,919), copolymers of L-glutamic acid and .gamma. ethyl-L-glutamate, non-degradable ethylene-vinyl acetate, degradable lactic acid-glycolic acid copolymers such as the LUPRON DEPOT (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Pharmaceutical compositions of the invention can be administered in combination therapy, i.e., combined with other agents. For example, the combination therapy can include an anti-MARCO antibody of the present invention combined with at least one other therapeutic agent. Examples of therapeutic agents that can be used in combination therapy are described in greater detail below.

The formulations to be used for in vivo administration must be sterile. This can be readily accomplished by filtration through sterile filtration membranes. Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for an anti-MARCO antibody of the invention include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks.

Alternatively, antibody can be administered as a sustained release formulation, in which case less frequent administration is required. Dosage and frequency vary depending on the half-life of the antibody in the patient. In general, human antibodies show the longest half-life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an anti-MARCO antibody of the invention preferably results in a decrease in severity of disease symptoms, an increase in frequency and duration of disease symptom-free periods, or a prevention of impairment or disability due to the disease affliction. For example, for the treatment of tumors, a "therapeutically effective dosage" preferably inhibits cell growth or tumor growth or metastasis by at least about 20%, more preferably by at least about 40%, even more preferably by at least about 60%, and still more preferably by at least about 80% relative to untreated subjects. The ability of an agent or compound to inhibit tumor growth can be evaluated in an animal model system predictive of efficacy in human tumors. Alternatively, this property of a composition can be evaluated by examining the ability of the compound to inhibit, such inhibition in vitro by assays known to the skilled practitioner. A therapeutically effective amount of a therapeutic compound can decrease tumor size, metastasis, or otherwise ameliorate symptoms in a subject. One of ordinary skill in the art would be able to determine such amounts based on such factors as the subject's size, the severity of the subject's symptoms, and the particular composition or route of administration selected.

In another aspect, the instant disclosure provides a pharmaceutical kit of parts comprising an anti-MARCO antibody and an anti-CTLA-4 and/or anti-PD-1 antibody. The kit may also further comprise instructions for use in the treatment of a hyperproliferative disease (such as cancer as described herein). In another embodiment, the anti-MARCO and/or anti-CTLA-4 and/or anti-PD-1 antibodies may be co-packaged in unit dosage form. IDO inhibitors may also be combined with the above treatments to further enhance the anti-tumor activity of anti-MARCO antibody treatment.

In certain embodiments, two or more monoclonal antibodies with different binding specificities (e.g., anti-MARCO and anti-CTLA-4) are administered simultaneously, in which case the dosage of each antibody administered falls within the ranges indicated. Antibody can be administered as a single dose or more commonly can be administered on multiple occasions. Intervals between single dosages can be, for example, weekly, monthly, every three months or yearly. Intervals can also be irregular as indicated by measuring blood levels of antibody to the target antigen in the patient.

A composition of the invention can be administered via one or more routes of administration using one or more of a variety of methods known in the art. As will be appreciated by the skilled artisan, the route and/or mode of administration will vary depending upon the desired results. Preferred routes of administration for antibodies of the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, an antibody of the invention can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

Therapeutic compositions can be administered with medical devices known in the art. For example, a therapeutic composition of the invention can be administered with a needleless hypodermic injection device, such as the devices disclosed in U.S. Pat. Nos. 5,399,163, 5,383,851, 5,312,335, 5,064,413, 4,941,880, 4,790,824, and 4,596,556. Examples of well-known implants and modules useful in the present invention include those described in U.S. Pat. Nos. 4,487,603, 4,486,194, 4,447,233, 4,447,224, 4,439,196, and 4,475,196. These patents are incorporated herein by reference. Many other such implants, delivery systems, and modules are known to those skilled in the art.

Uses and Methods

The antibodies, antibody compositions and methods of the present invention have numerous in vitro and in vivo utilities involving, for example, detection of MARCO or enhancement of immune response.

Treatment

As disclosed herein, selectively targeting MARCO-expressing TAMs in the tumor stroma was sufficient to shift the anti-inflammatory, pro-tumorigenic and pro-metastatic TME to a more pro-inflammatory and less supportive TME for tumor progression. As a result, tumor growth and metastatic spread was inhibited. Accordingly, targeting MARCO-expressing TAMs by antibodies of this invention can enhance the immune response to cancerous cells in a patient. This approach is particularly suitable for treatment of tumors characterized by presence of MARCO expression on TAMs in the tumor microenvironment.

Accordingly, in one aspect, the present invention relates to treatment of a subject in vivo using an anti-MARCO antibody such that growth and/or metastasis of cancerous tumors is inhibited. In one embodiment, the invention provides a method of inhibiting growth and/or restricting metastatic spread of tumor cells in a subject, comprising administering to the subject a therapeutically effective amount of an anti-MARCO antibody, or antigen-binding portion thereof. Preferably, the antibody is a human anti-MARCO antibody (such as any of the human anti-human MARCO antibodies described herein). Additionally or alternatively, the antibody may be a chimeric or humanized anti-MARCO antibody. An anti-MARCO antibody may be used alone to inhibit the growth of cancerous tumors. Alternatively, an anti-MARCO antibody may be used in conjunction with other immunogenic agents, standard cancer treatments, or other antibodies, as described herein.

Preferred cancers whose growth or metastatic spread may be inhibited using the antibodies of the invention include cancers characterized by presence of MARCO expression on TAMs in their tumor microenvironment. Non-limiting examples of preferred cancers for treatment include breast cancer, ovarian cancer, melanoma (e.g., metastatic malignant melanoma), renal cancer (e.g. clear cell carcinoma), prostate cancer (e.g. hormone refractory prostate adenocarcinoma), colon cancer and lung cancer (e.g. non-small cell lung cancer). Additionally, the invention includes refractory or recurrent malignancies whose growth may be inhibited using the antibodies of the invention.

Examples of other cancers that may be treated using the methods of the invention include bone cancer, pancreatic cancer, skin cancer, cancer of the head or neck, cutaneous or intraocular malignant melanoma, uterine cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The present invention is also useful for treatment of metastatic cancers that have MARCO expression on TAMs in their tumor microenvironment.

In a preferred embodiment, the antibodies of the present invention can be administered to human subjects, e.g., in vivo, to reprogram TAMs into a pro-inflammatory phenotype thereby rendering a tumor immunogenic. Accordingly, in one aspect, the invention provides a method of modifying TAMs in a subject comprising administering to the subject the antibody, or antigen-binding portion thereof, of the invention such that the TAM in the subject is modified.

As used herein, the term "subject" is intended to include human and non-human animals. Non-human animals includes all vertebrates, e.g. mammals and non-mammals, such as non-human primates, sheep, dogs, cats, cows, horses, chickens, amphibians, and reptiles, although mammals are preferred, such as non-human primates, sheep, dogs, cats, cows and horses. Preferred subjects include human patients in need of enhancement of an immune response. The methods are particularly suitable for treating human patients having a disorder that can be treated by augmenting the immune response.

MARCO targeting may also be combined with standard cancer treatments. For example, MARCO targeting may be effectively combined with chemotherapeutic regimes. In these instances, it may be possible to reduce the dose of chemotherapeutic reagent administered (Mokyr, M. et al. (1998) Cancer Research 58: 5301-5304). An example of such a combination is an anti-MARCO antibody in combination with decarbazine for the treatment of melanoma. Another example of such a combination is an anti-MARCO antibody in combination with interleukin-2 (IL-2) for the treatment of melanoma. Other combination therapies that may result in synergy with MARCO targeting through cell death are radiation, surgery, and hormone deprivation. Angiogenesis inhibitors may also be combined with MARCO targeting.

Other antibodies which may be used to activate host immune responsiveness can be used in combination with anti-MARCO. These include molecules on the surface of dendritic cells which activate DC function and antigen presentation. For example, anti-CD40 antibodies are able to substitute effectively for T cell helper activity (Ridge, J. et al. (1998) Nature 393: 474-478) and can be used in conjunction with MARCO antibodies (Ito, N. et al. (2000) Immunobiology 201 (5) 527-40). Similarly, activating antibodies to T cell costimulatory molecules such as CTLA-4 (e.g., U.S. Pat. No. 5,811,097), OX-40 (Weinberg, A. et al. (2000) Immunol 164: 2160-2169), 4-1BB (Melero, I. et al. (1997) Nature Medicine 3: 682-685 (1997), PD-1 (U.S. Pat. No. 8,008,449), PD-1L (U.S. Pat. Nos. 7,943,743 and 8,168,179) and ICOS (Hutloff, A. et al. (1999) Nature 397: 262-266) may also provide for increased levels of T cell activation.

In one embodiment, the present invention provides a method for treating a tumor, comprising administering an anti-MARCO antibody and an anti-CTLA-4 antibody to a subject. In further embodiments, the anti-MARCO antibody is administered at a subtherapeutic dose, the anti-CTLA-4 antibody is administered at a subtherapeutic dose, or both are administered at a subtherapeutic dose. In another embodiment, the present invention provides a method for altering an adverse event associated with treatment of a hyperproliferative disease with an immunostimulatory agent, comprising administering an anti-MARCO antibody and a subtherapeutic dose of anti-CTLA-4 antibody to a subject. In certain embodiments, the subject is human.

In another example, an anti-MARCO antibody can be used in conjunction with anti-neoplastic antibodies, such as RITUXAN (rituximab), HERCEPTIN (trastuzumab), BEXXAR (tositumomab), ZEVALIN (ibritumomab), CAMPATH (alemtuzumab), LYMPHOCIDE (eprtuzumab), AVASTIN (bevacizumab), and TARCEVA (erlotinib), and the like.

Detection

As mentioned above, one of the unexpected discoveries of this invention is that the pattern recognition scavenger receptor MARCO defines a subtype of TAMs and its expression is linked to poor clinical outcome in certain cancers. Thus, MARCO and related agents (e.g., antibodies and kits) can be used in determining whether a subject has, or is at risk of having, a cellular proliferative disorder mentioned above. Alternatively, they can be used for determining a prognosis of such a disorder in a subject. These subjects can be treated with the treatment methods of this invention. Thus, the detection agents can be included in a companion diagnosis kit for the treatment.

Accordingly, the invention provides methods for detecting the presence of human MARCO antigen in a sample, or measuring the amount of human MARCO antigen, comprising contacting the sample, and a control sample, with an anti-MARCO antibody, or an antigen-binding portion thereof, which specifically binds to human MARCO, under conditions that allow for formation of a complex between the antibody or portion thereof and human MARCO. The formation of a complex is then detected, wherein a complex formation between the sample and the antibody as compared to the control sample is indicative the presence of human MARCO antigen in the sample.

In one aspect, the present invention relies upon the ability of anti-MARCO antibody to identify cancer with poor clinical outcome. Accordingly, the present invention provides assays or methods of diagnosing and evaluating a biological sample, e.g., a surgically or endoscopically resected tissue or fluid sample using anti-MARCO antibody or its equivalent for various malignancies. This evaluation of MARCO expression on TAMs in their tumor microenvironment is a useful tool to identify cancer with poor clinical outcome and help clinical decision-making.

The detection methods can be used to detect MARCO-expressing TAM in a biological sample in vitro as well as in vivo. In vitro techniques for detection include ELISAs, immuocytochemistry, immuohistochemistry immunoprecipitati ons, immunofluorescence, EIA, RIA, Western blotting, and flow cytometry analysis. In vivo techniques for detection of the protein include introducing into a subject a labeled anti-MARCO antibody. For example, the antibody can be labeled with a detectable substance as described above. The presence and location of the detectable substance in a subject can be detected by standard imaging techniques. In the latter case, human or humanized antibodies are preferred so as to minimize any side effects.

Kits

In a further embodiment, the present invention provides a kit for detecting MARCO expression in a sample. A kit comprises one or more antibodies that are specific for MARCO and means for determining binding of the antibody to the MARCO in the sample. The kit may also comprise packaging material comprising a label that indicates that the one or more antibody of the kit can be used for the cancer diagnosis or prognosis. Other components such as buffers, controls, detection reagents, and the like known to those of ordinary skill in art may be included in such kits.

A kit may contain, in an amount sufficient for at least one assay, any combination of the components described herein, and may further include instructions recorded in a tangible form for use of the components. In some applications, one or more reaction components may be provided in pre-measured single use amounts in individual, typically disposable, tubes or equivalent containers. With such an arrangement, the sample to be tested for the presence of a target can be added to individual tubes or substrates and assay carried out directly. The amount of a component supplied in the kit can be any appropriate amount, and may depend on the target market to which the product is directed. General guidelines for determining appropriate amounts may be found in, for example, Joseph Sambrook and David W. Russell, Molecular Cloning: A Laboratory Manual, 3rd edition, Cold Spring Harbor Laboratory Press, 2001; and Frederick M. Ausubel, Current Protocols in Molecular Biology, John Wiley & Sons, 2003.

The kits of the invention can comprise any number of additional reagents or substances that are useful for practicing a method of the invention. Such substances include, but are not limited to: anticoagulants (e.g., EDTA and heparin), reagents (including buffers) for processing (e.g., lysis) of cells, divalent cation chelating agents or other agents that inhibit unwanted proteases, control antibodies for use in ensuring that the components of reactions are functioning properly, and wash solutions. The kits of the invention can be provided at any temperature. For example, for storage of kits containing protein components or complexes thereof in a liquid, it is preferred that they are provided and maintained below 0° C., preferably at or below −20° C., or otherwise in a frozen state.

As disclosed herein, a number of ranges of values are provided. It is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention.

Definitions

The terms "peptide," "polypeptide," and "protein" are used herein interchangeably to describe the arrangement of amino acid residues in a polymer. A peptide, polypeptide, or protein can be composed of the standard 20 naturally occurring amino acid, in addition to rare amino acids and synthetic amino acid analogs. They can be any chain of amino acids, regardless of length or post-translational modification (for example, glycosylation or phosphorylation).

A "recombinant" peptide, polypeptide, or protein refers to a peptide, polypeptide, or protein produced by recombinant DNA techniques; i.e., produced from cells transformed by an exogenous DNA construct encoding the desired peptide. A "synthetic" peptide, polypeptide, or protein refers to a peptide, polypeptide, or protein prepared by chemical synthesis. The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Within the scope of this invention are fusion proteins containing one or more of the afore-mentioned sequences and a heterologous sequence. A heterologous polypeptide, nucleic acid, or gene is one that originates from a foreign species, or, if from the same species, is substantially modified from its original form. Two fused domains or sequences are heterologous to each other if they are not adjacent to each other in a naturally occurring protein or nucleic acid.

An "isolated" peptide, polypeptide, or protein refers to a peptide, polypeptide, or protein that has been separated from other proteins, lipids, and nucleic acids with which it is naturally associated. The polypeptide/protein can constitute at least 10% (i.e., any percentage between 10% and 100%, e.g., 20%, 30%, 40%, 50%, 60%, 70%, 80%, 85%, 90%, 95%, and 99%) by dry weight of the purified preparation. Purity can be measured by any appropriate standard method, for example, by column chromatography, polyacrylamide gel electrophoresis, or HPLC analysis. An isolated polypeptide/protein described in the invention can be purified from a natural source, produced by recombinant DNA techniques, or by chemical methods.

An "antigen" refers to a substance that elicits an immunological reaction or binds to the products of that reaction. The term "epitope" refers to the region of an antigen to which an antibody or T cell binds.

As used herein, "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

As used herein, "antibody fragments", may comprise a portion of an intact antibody, generally including the antigen binding and/or variable region of the intact antibody and/or the Fc region of an antibody which retains FcR binding capability. Examples of antibody fragments include linear antibodies; single-chain antibody molecules; and multispecific antibodies formed from antibody fragments. Preferably, the antibody fragments retain the entire constant region of an IgG heavy chain, and include an IgG light chain.

As used herein, the term "Fc fragment" or "Fc region" is used to define a C-terminal region of an immunoglobulin heavy chain. A "native sequence Fc region" comprises an amino acid sequence identical to the amino acid sequence of an Fc region found in nature. A "variant Fc region" as appreciated by one of ordinary skill in the art comprises an amino acid sequence which differs from that of a native sequence Fc region by virtue of at least one "amino acid modification." Preferably, the variant Fc region has at least one amino acid substitution compared to a native sequence Fc region or to the Fc region of a parent polypeptide, e.g., from about one to about ten amino acid substitutions, and preferably from about one to about five amino acid substitutions in a native sequence Fc region or in the Fc region of the parent polypeptide. The variant Fc region herein will preferably possess at least about 70% homology with a native sequence Fc region and/or with an Fc region of a parent polypeptide, and more preferably at least about 90% homology therewith, more preferably at least about 95% homology therewith, even more preferably, at least about 99% homology therewith.

The terms "Fc receptor" or "FcR" are used to describe a receptor that binds to the Fc region of an antibody. The preferred FcR is a native sequence human FcR. Moreover, a preferred human FcR is one which binds an IgG antibody (a gamma receptor) and includes receptors of the human FcγRI, Fc γRII, and FcγRIII subclasses, including allelic variants and alternatively spliced forms of these receptors. FcγRII receptors include FcγRIIa (an "activating receptor") and FcγRIIb (an "inhibiting receptor"), which have similar amino acid sequences that differ primarily in the cytoplasmic domains thereof. Activating receptor FcγRIIa contains an immunoreceptor tyrosine-based activation motif (ITAM) in its cytoplasmic domain Inhibiting receptor FcγRIIb contains an immunoreceptor tyrosine-based inhibition motif (ITIM) in its cytoplasmic domain (see Daron, Annu Rev Immunol, 15, 203-234 (1997); FcRs are reviewed in Ravetch and Kinet, Annu Rev Immunol, 9, 457-92 (1991); Capel et al., Immunomethods, 4, 25-34 (1994); and de Haas et al., J Lab Clin Med, 126, 330-41 (1995), each of which is incorporated herein by reference).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler and Milstein, Nature, 256, 495-497 (1975), which is incorporated herein by reference, or may be made by recombinant DNA methods (see, e.g., U.S. Pat. No. 4,816,567, which is incorporated herein by reference). The monoclonal antibodies may also be isolated from phage antibody libraries using the techniques described in Clackson et al., Nature, 352, 624-628 (1991) and Marks et al., J Mol Biol, 222, 581-597 (1991), for example, each of which is incorporated herein by reference.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; Morrison et al., Proc Natl Acad Sci USA, 81, 6851-6855 (1984); Neuberger et al., Nature, 312, 604-608 (1984); Takeda et al., Nature, 314, 452-454 (1985); International Patent Application No. PCT/GB85/00392, each of which is incorporated herein by reference).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR residues are those of a human immunoglobulin sequence. The humanized antibody optionally also will comprise at least a portion of an immunoglobulin constant region (Fc), typically that of a human immunoglobulin. For further details, see Jones et al., Nature, 321, 522-525 (1986); Riechmann et al., Nature, 332, 323-329 (1988); Presta, Curr Op Struct Biol, 2, 593-596 (1992); U.S. Pat. No. 5,225,539, each of which is incorporated herein by reference.

Human antibodies refer to any antibody with fully human sequences, such as might be obtained from a human hybridoma, human phage display library or transgenic mouse expressing human antibody sequences.

The term "pharmaceutical composition" refers to the combination of an active agent with a carrier, inert or active, making the composition especially suitable for diagnostic or therapeutic use in vivo or ex vivo.

As used herein, "pharmaceutically acceptable carrier" includes any and all solvents, dispersion media, coatings, antibacterial and antifungal agents, isotonic and absorption delaying agents, and the like that are physiologically compatible. A "pharmaceutically acceptable carrier," after administered to or upon a subject, does not cause undesirable physiological effects. The carrier in the pharmaceutical composition must be "acceptable" also in the sense that it is compatible with the active ingredient and can be capable of stabilizing it. One or more solubilizing agents can be utilized as pharmaceutical carriers for delivery of an active agent. Examples of a pharmaceutically acceptable carrier include, but are not limited to, biocompatible vehicles, adjuvants, additives, and diluents to achieve a composition usable as a dosage form. Examples of other carriers include colloidal silicon oxide, magnesium stearate, cellulose, and sodium lauryl sulfate. Additional suitable pharmaceutical carriers and diluents, as well as pharmaceutical necessities for their use, are described in Remington's Pharmaceutical Sciences. Preferably, the carrier is suitable for intravenous, intramuscular, subcutaneous, parenteral, spinal or epidermal administration (e.g., by injection or infusion). The therapeutic compounds may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) J. Pharm. Sci. 66:1-19).

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, and toxins such as small molecule toxins or enzymatically active toxins of bacterial, fungal, plant or animal origin, including fragments and/or variants thereof.

A "chemotherapeutic agent" is a chemical compound useful in the treatment of cancer. Examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as the enediyne antibiotics (e.g. calicheamicin, see, e.g., Agnew Chem. Intl. Ed. Engl. 33:183-186 (1994); dynemicin, including dynemicin A; an esperamicin; as well as neocarzinostatin chromophore and related chromoprotein enediyne antibiotic chromomophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; podophyllinic acid; 2-ethylhydrazide; procarbazine; PSK®; razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (TAXOTERE®, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above.

As used herein, "treating" or "treatment" refers to administration of a compound or agent to a subject who has a disorder or is at risk of developing the disorder with the purpose to cure, alleviate, relieve, remedy, delay the onset of, prevent, or ameliorate the disorder, the symptom of the disorder, the disease state secondary to the disorder, or the predisposition toward the disorder.

An effective amount refers to the amount of an active compound/agent that is required to confer a therapeutic effect on a treated subject. Effective doses will vary, as recognized by those skilled in the art, depending on the types of conditions treated, route of administration, excipient usage, and the possibility of co-usage with other therapeutic treatment. A therapeutically effective amount of a combination to treat a neoplastic condition is an amount that will cause, for example, a reduction in tumor size, a reduction in the number of tumor foci, or slow the growth of a tumor, as compared to untreated animals.

The term "about" generally refers to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

The term "biological sample" refers to a sample obtained from an organism (e.g., patient) or from components (e.g., cells) of an organism. The sample may be of any biological tissue, cell(s) or fluid. The sample may be a "clinical sample" which is a sample derived from a subject, such as a human patient. Such samples include, but are not limited to, saliva, sputum, blood, blood cells (e.g., white cells), amniotic fluid, plasma, semen, bone marrow, and tissue or fine needle biopsy samples, urine, peritoneal fluid, and pleural fluid, or cells therefrom. Biological samples may also include sections of tissues such as frozen sections taken for histological purposes. A biological sample may also be referred to as a "patient sample." A biological sample may also include a substantially purified or isolated protein, membrane preparation, or cell culture.

As used herein, the term "contacting" and its variants, when used in reference to any set of components, includes any process whereby the components to be contacted are mixed into same mixture (for example, are added into the same compartment or solution), and does not necessarily require actual physical contact between the recited components. The recited components can be contacted in any order or any combination (or subcombination), and can include situations where one or some of the recited components are subsequently removed from the mixture, optionally prior to addition of other recited components. For example, "contacting A with B and C" includes any and all of the following situations: (i) A is mixed with C, then B is added to the mixture; (ii) A and B are mixed into a mixture; B is removed from the mixture, and then C is added to the mixture; and (iii) A is added to a mixture of B and C. "Contacting a template with a reaction mixture" includes any or all of the following situations: (i) the template is contacted with a first component of the reaction mixture to create a mixture; then other components of the reaction mixture are added in any order or combination to the mixture; and (ii) the reaction mixture is fully formed prior to mixture with the template.

EXAMPLES

Example 1

This example describes materials and methods used in Examples 2-6 below.

Cell Culture

The B16 Luciferase transfected (B16-luc) mouse melanoma cell line (kind gift from Dr. K. Weilbaecher, Washington University in St. Louis, USA) was cultured in complete medium (DMEM supplemented with 2 mM L-glutamine, 10 mM HEPES, and 10% heat-inactivated FCS) and selective expression of the plasmid bearing the luciferase gene was maintained by addition of 100 µg/ml Geneticin (G418) once a week during propagation. All cells used for the individual repeats of the experiment originate from the same early passage stock and are cultured for ca 1 week before in vivo administration. The 4T1 mammary carcinoma cell line (Barbara Ann Karmanos Cancer Institute, Detroit, USA) was cultured in RPMI-1640 medium supplemented with 10% FBS, 1% Penicillin-Streptomycin and 1% Glutamine. The IC-21 peritoneal macrophage cell line (ATCC) was cultured in in RPMI-1640 medium supplemented with 10% FBS, 1% Penicillin-Streptomycin and 1% Glutamine. The rat anti-MARCO IgG1 mAb hybridoma ED31 was a generous gift from Prof. G. Kraal. For generation of in vitro bone marrow derived macrophages, bone marrow was collected by flushing the femurs of 8-10-week-old C57BL/6 or MARCO KO mice with cold DMEM. After collection, red blood cells were lysed and the cells were washed twice in PBS. To induce macrophage differentiation cells were resuspended in DMEM supplemented with 20% FCS and 20% M-CSF conditioned medium collected from 3-4 day cultures of mouse L929 fibroblasts secreting M-CSF. The cells were plated in different sized vessels depending on the application. On day 3 half of the volume was replaced with fresh DMEM/M-CSF, and on day 6 the entire volume was replenished. On day 10 of in vitro culture the cells were polarized using standard conditions as reported by Mosser et al. (29) More specifically, M1 classical activation was induced by addition of 20 ng/ml IFNγ and 10 ng/ml LPS, M2 alternative activation was induced by addition of 20 ng/ml IL-4 and 20 ng/ml IL-13, for TAMs a supernatant from in vitro cultures of B16 or 4T1 cells was applied and for M0 only DMEM 10% FBS was added. The cytokines were purchased from R&D SYSTEMS. After polarization the cells were phenotyped, stimulated with mAbs and used in different assays.

Animal Studies

Mice were maintained at the Microbiology Tumor and Cell biology animal facility at Karolinska Institute and the experiments were approved by the local ethical committee (the North Stockholm district court). Wildtype C57BL/6, Balb/c (TACONIC) and MARCO KO and FcRIIb KO (TACONIC) on C57BL/6 mixed background mice were kept and bred under pathogen-free conditions according to local ethical guidelines. FcRa null (Smith PNAS 2012), Fcer1g$^{-/-}$ (Takai Cell 1994), humanized FcγR mice (Smith PNAS 2012) from Dr. JV Ravetch's laboratory at Rockefeller University, NYC, USA were used in B16 tumor experiments. Mice at the age of 8-10 weeks were injected s.c in the right flank with 1×10$^5$ B16 Luciferase transfected (B16-luc) cells in BD Matrigel (later taken over by CORNING). At days 3, 6 and 9 of the experimental setup, mice were injected i.v with 50 or 100 µg of anti-MARCO mAb (rat IgG1, clone ED31), 200 µg TA99 mAb (mouse IgG2a) and or 100 µg anti-CTLA-4 mAb (9D9) from Bioxcell. The anti-CTLA-4 mAb was used in combination with 1×10$^6$ irradiated (150Gy) B16-BL6 cells expressing GM-CSF (GVAX) that were injected s.c in the contralateral flank. The animals were imaged using intravital imaging (IVIS) at the same timepoints. For the 4T1 model and the B16 model survival studies the tumors were measured manually every second day for the entire duration of the experiments. On day 10 of the experimental setup the animals were sacrificed and tumors, spleens and lymph nodes were collected for further analyses. Balb/c mice were injected in the mammary fat pad with 2×10$^5$ syngeneic 4T1 mammary adenocacinoma cells and treated with 100 µg of anti-MARCO mAb on days 0 and 3, and thereafter with 50 µg every third day. Mice were sacrificed on day 21 and primary tumors, lung metastases, spleens, draining and non-draining lymph nodes were assessed.

Cloning of Fc-Modified Variants of the Rat Anti MARCO IgG1 ED31 mAb

Cloning of the rat (anti-MARCO) IgG CDRs from ED31 hybridoma cDNA was performed using RACE. A list of the primers used is listed below.

```
Arg 1:
FP,
                                        (SEQ ID No: 6)
5'-CCACAGTCTGGCAGTTGGAAG-3'

RP,
                                        (SEQ ID No: 7)
5'-GGTTGTCAGGGGAGTGTTGATG-3'

Retn1a (Fizz-1):
FP,
                                        (SEQ ID No: 8)
5'-CCTGCTGGGATGACTGCTA-3'

RP,
                                        (SEQ ID No: 9)
5'-TGGGTTCTCCACCTCTTCAT-3'

H2-Ab1 (MHC II):
FP,
                                        (SEQ ID No: 10)
5'-TTTGCTTTCTGAAGGGGGCA-3'

RP,
                                        (SEQ ID No: 11)
5'-TCGCCCATGAACTGGTACAC-3'

Chi3l3 (Ym1):
FP,
                                        (SEQ ID No: 12)
5'-GCCACTGAGGTCTGGGATGC-3'

RP,
                                        (SEQ ID No: 13)
5'-TCCTTGAGCCACTGAGCCTTC-3'

MARCO:
FP,
                                        (SEQ ID No: 14)
5'-GGCACCCCAAGGGAGACAAA-3'

RP,
                                        (SEQ ID No: 15)
5'-TCCCTTCATGCCATGTC-3'

Rpl13a:
FP,
                                        (SEQ ID No: 16)
5'-GAGGTCGGGTGGAAGTACCA-3'

RP,
                                        (SEQ ID No: 17)
5'-TGCATCTTGGCCTTTTCCTT-3'

FcgRIIb:
FP,
                                        (SEQ ID No: 18)
5'-CTGAGGCTGAGAATACGATC-3'

RP,
                                        (SEQ ID No: 19)
5'-GTGGATCGATAGCAGAAGAG-3'
```

```
NOS2:
FP,
                                         (SEQ ID No: 20)
5'-CGAAACGCTTCACTTCCAA-3'

RP,
                                         (SEQ ID No: 21)
5'-TGAGCCTATATTGCTGTGGCT-3'
```

Antibody Production and Purification

Antibody Expression Vectors were Transfected into Competent E. coli Cells and cultured to single clones that were screened for the production of the correct DNA construct. The chosen clones were expanded for plasmid purification. Plasmids were transfected into 293T HEK cells for production of the different mAbs. Culture supernatants were collected and the antibodies were isolated by standard protein purification techniques using G protein specific separation columns.

Lung Tumor Colony Formation Assay

Lungs were harvested in PBS+10% FBS and dissociated in STEMPRO Accutase medium supplemented with TrypLE at a 1:1 ratio and 1 mg/ml DNAse in 6-well plates. They were subsequently dissected into small pieces and incubated at 37° C. for 20 minutes. The tissue was further disturbed by passaging through a syringe (without the needle) and lastly through a syringe with a needle for further dissociation. The cell suspension was filtered through a 70 µm cell-strainer followed by treatment with erythrocyte lysis buffer. The lung cells were resuspended in RPMI-1640 medium containing 60 µM/L 6-thioguanine (SIGMA) and seeded in 10 cm plates. The culture medium was changed after 4-5 days. On day 10, the cells were washed and fixed in formaldehyde. After washing with distilled $H_2O$, the cells were stained with haematoxylin for 5 min and the plates were dried upside-down, after which the number of microcolonies was counted.

Immunofluorescence

Murine tumors were cryopreserved in OCT medium NEG 50 (THERMO SCIENTIFIC) and 8 mm-thick sections were cut using a cryostat microtome. After overnight drying the slides were fixed in acetone and stored at −80° C. Before staining slides were blocked with 5% goat serum (DAKOCYTOMATION) in PBS. The following antibodies were used: rat anti-MARCO produced by the ED31 hybridoma and conjugated to AF555 (LIFE TECHNOLOGIES), goat anti-rat IgG AF555 (LIFE TECHNOLOGIES), anti-F4/80 AF647 and anti-CD11b AF488 (BIOLEGEND). Slides were mounted with Prolong Diamond DAPI-containing mounting medium. Human breast carcinoma cryosections were fixed with 4% PFA followed by treatment with 0.1% Triton-X100. After blocking with goat serum primary Abs were incubated overnight at +4° C., while secondary Abs were incubated for 1 h at RT in 0.1% BSA PBS solution. Samples were stained with mouse-anti-human E-cadherin Ab (BIOLEGEND), mouse-anti-human anti-CD68 AF488 (SANTA CRUZ BIOTECHNOLOGY) and rabbit-anti-human anti-MARCO Ab (ABCAM) and detected using goat-anti-mouse IgG(H+L) AF488 and goat-anti-rabbit IgG(H+L) AF555 (LIFE TECHNOLOGIES). Images were collected using a confocal microscope (LEICA TCS SP5 X or LSM-700; CARL ZEISS MICROIMAGING Inc.). Confocal stack images were recorded with the LSM Image software and used to generate 3D projections.

Cell Staining on Glass Coverslips or Chamber Wells

Cells were seeded in wells for overnight attachment. Prior to antibody incubation, the cells were incubated for 10 min in ice cold DMEM, 1% BSA, 20 mM HEPES. The cells were stained with anti-CD11b A488, anti-F4/80 A647 and anti-MARCO AF555 (ED31) for 30 minutes on ice in dark. The wells were washed thoroughly with 1% BSA/PBS and the cells were fixed with 4% PFA for 20 minutes at room temperature. The cells were washed with 1% BSA/PBS and mounted with PROLONG DIAMOND DAKO mounting medium.

Intravital Imaging System (IVIS)

Animals were imaged in groups of 5 using an IVIS Spectrum CT (PERKIN ELMER). Mice were injected s.c with $1 \times 10^5$ B16-luc cells in BD Matrigel. The animals were weighed and shaved locally at the injection site before imaging. The mice were subsequently injected i.p with 15 mg/g body weight of the substrate D-Luciferin Potassium salt (PERKIN ELMER). After determining the kinetics curve of luciferin breakdown for the B16-luc system, the optimal imaging time point was determined at around 15 minutes after substrate administration. As the time point of maximal bioluminescence read out fluctuated with tumor size over the course of the experiment, an imaging sequence of 6 segments with 5 minutes delay was captured per imaging session. Measurements were taken on days 3, 6 and 9, respectively, of the experimental setup. The mice were anesthetized with isofluorane for the procedure.

Tumor Dissociation Protocol

B16-luc tumors were harvested in cold RPMI on day 10. They were finely cut into pieces using surgical scalpels and further enzymatically dissociated through the addition of 200 µg/ml DNase I (ROCHE), 200 µg/ml hyaluronidase (SIGMA), 66 µg/ml Liberase TL (ROCHE) and 1M HEPES for 30-45 min at 37° C. with stirring. After 20 minutes of incubation 0.1 M EDTA was added to avoid clumping. The samples were incubated for an additional 10 minutes on ice to allow isolation of macrophages and dendritic cells. Thereafter the preparations were passed through a 100 µm filter strainer and washed thoroughly with HBSS buffer supplemented with 2% FCS, 20 mM HEPES and 5 mM EDTA. Finally the cells were resuspended in PBS and stained for flow cytometry. In some cases the mouse tumor dissociation kit from Miltenyi Biotech was used, with no difference in the amount or quality of the dissociated cells. 4T1 tumors were dissociated using the MILTENYI mouse tumor dissociation kit according to the manufacturers' instructions and using the GENLTE MACS dissociator (MILTENYI BIOTECH).

Flow Cytometry

Single-cell suspensions of tumors were prepared and erythrocytes were lysed. Non-specific labeling was blocked with anti-CD16/32 (Fc Block) (BIOLEGEND) before specific labeling. LIVE/DEAD Aqua staining was used to remove dead cells. Extracellular proteins were labeled and after several washing steps, fixation and permeabilization (buffers from BIOLEGEND) followed. For intracellular FoxP3 staining the manufacturer's protocol was followed (INVITROGEN). All FACS plots depict log 10 fluorescence. Cells were stained with the following rat-anti-mouse Abs from BioLegend: Anti-TCRβ APC, anti-NK.1.1 PerCP-Cy5.5, anti-CD4 FITC, anti-CD8 PE, anti-CD45R Pacific blue, anti-CD45 APC-Cy7, anti-CD11b PECy7, anti-F4/80 APC-Cy7 & Pacific blue, anti-CD11c PerCP-Cy5.5 & PE, anti-Gr-1 Pacific blue, anti-Ly6G AF488, anti-Ly6C AF647, anti-MHCII PerCP-Cy5.5, anti-CD43 PE, anti-CD206 AF488, anti-CD124 PE, anti-CD68 AF488, anti-CD86 FITC, anti-CD115 PE, anti-CD49d PE, anti-IgD PerCP-Cy5.5, anti-CD45 AF700, anti-B220-APC Cy7, anti-CD38 PE-Cy7, anti-B220-FITC, anti-CD8 FITC, anti-FoxP3 PE, anti-CD49b APC, anti-CD4 pacific blue, anti-CD3-biotin, and streptavidin-Qdot605. Anti-GL7 FITC and anti-CD95 PE were purchased from BD. 7AAD or Live/Dead marker Aqua AmCyan (LIFE TECHNOLOGIES) were used for live-dead cell discrimination. The samples were analyzed using a BD LSR Fortessa X-20 cytometer and analyzed with FlowJo software.

Flow Cytometry-Based Sorting of Macrophage Populations from Tumors

After tumor dissociation CD45$^+$ cells were positively selected from the tumor lysate by magnetic assisted cell sorting. Live CD45$^+$CD11b$^+$ Ly6G$^-$ cells were sorted using a BD FACS Aria Fusion™ cell sorter into Ly6C$^{hi}$ MHCII$^{lo}$, Ly6C$^{int}$ MHCII$^{hi}$, Ly6C$^{lo}$ MHC$^{hi}$ and Ly6C$^{lo}$ MHCII$^{lo}$ subsets.

Quantitative PCR (qPCR)

Custom designed primers (SIGMA) for qPCR were used to determine expression of a variety of macrophage polarization and cytokine genes (h2-ab1, fcgr2b, arg1, marco, nos2, fizz/retnla, ym1/chi3l3 and rpl13a as a housekeeping gene). In vitro cultured cells were lysed in RLT buffer with 1% β-mercaptoethanol (LIFE TECHNOLOGIES) and RNA preparation was performed using the QIAGEN RNEASY micro/mini plus kit. cDNA was synthesized using iScript (BIORAD) under standard conditions. qPCR using SYBR-Green (BIORAD) was performed on a CFX96 Real time cycler (BIORAD) and analyzed according to the Livak method for relative expression.

Statistics

Data were analyzed by unpaired Mann-Whitney U t-test to compare two groups. A P value of <0.05% was considered to be statistically significant.

Bioinformatics and Medical Statistics

TCGA breast cancer data set: Clinical data from the TCGA invasive breast carcinoma dataset (provisional) was downloaded from the TCGA data portal (https://tcga-data.nci.nih.gov/tcga/) on 11 Dec. 2013 and included data for 1148 cases. Unaligned RNAseq data from the TCGA dataset was subsequently downloaded (June 2014) after approval from the TCGA data access committee (N=1126, all available cases with unaligned data). A total of 1073 cases were available with both unaligned RNAseq data and clinical data. Of these, 35 observations were excluded as potential outliers based on inspection of Principal Component Analysis scores and residuals. A total of 885 of the 1038 cases had molecular subtype (PAM50) assignments available. All remaining cases classified as Normal-like subtype (N=105) were excluded as the clinical relevance for this subtype has been questioned (P. Eroles, A. Bosch, J. A. Perez-Fidalgo, A. Lluch, Molecular biology in breast cancer: intrinsic subtypes and signaling pathways. Cancer treatment reviews 38, 698 (October, 2012), leaving 780 samples for further analysis.

Tissue Collection, RNA Extraction, RNA Library construction and sequencing for the KI breast cancer data set: Tumor tissues from 255 patients diagnosed with breast cancer between 2006 and 2010 at the Karolinska Hospital (Stockholm, Sweden) and 63 patients during 2012 at South General hospital in Stockholm (Sweden) was snap-frozen on dry ice and stored at −80° C. RNA was extracted from fresh frozen tumors using AllPrep DNA/RNA/Protein mini kit (QIAGEN). RNA was assessed using bioanalyzer to ensure high quality (RIN>8). One μg of total RNA was used for rRNA depletion using RiboZero (ILLUMINA) and stranded RNAseq libraries were constructed using a TruSeq Stranded Total RNA Library Prep Kit (ILLUMINA). Sequencing was performed using an Illumina HiSeq 2500 at Science for Life Laboratories. In total the KI data set contained 318 cases with RNAseq data. Of these, 11 were excluded as potential outliers based on inspection of Principal Component scores and residuals, leaving 307 samples for analyses.

Bioinformatic pre-processing of RNAseq data: Standard Illumina adapters (AGATCGGAAGAGCACACGTCT-GAACTCCAGTCAC, SEQ ID No: 22) and AGATCG-GAAGAGCGTCG-TGTAGGGAAAGAGTGTA, SEQ ID No: 23) were trimmed using skewer version 0.1.117 (H. Jiang, R. Lei, S. W. Ding, S. Zhu, Skewer: a fast and accurate adapter trimmer for next-generation sequencing paired-end reads. BMC bioinformatics 15, 182 (2014)) with default parameters for both single end and paired end data. Alignment was conducted using STAR aligner version 2.4.0e (A. Dobin et al., STAR: ultrafast universal RNA-seq aligner. Bioinformatics 29, 15 (Jan. 1, 2013)) with the following parameters: "-outSAMmapqUnique 50", to set the mapping quality of uniquely mapped reads to 50; "-outSAMunmapped Within", to include unmapped reads in the resulting SAM file; "-chimSegmentMin 20" to require that a minimum of 20 bases maps to each end of a chimeric transcript (output in a separate file) and "-outSAMattributes NH HI AS nM NM MD XS" to include additional attributes in the SAM file. Gene expression estimates were calculated with HTSeq count version 0.6.0 (S. Anders, P. T. Pyl, W. Huber, HTSeq-a Python framework to work with high-throughput sequencing data. Bioinformatics 31, 166 (Jan. 15, 2015)) with the following parameters: "-stranded=no" for TCGA, since the TCGA Breast Cancer RNAseq data is non-stranded or "-stranded=reverse" for KI data, and "-mode=intersection-nonempty" for counting reads. The RNAseq count data were normalised using the TMM method (M. D. Robinson, A. Oshlack, A scaling normalization method for differential expression analysis of RNA-seq data. Genome biology 11, R25 (2010)) provided in the edgeR package (M. D. Robinson, D. J. McCarthy, G. K. Smyth, edgeR: a Bioconductor package for differential expression analysis of digital gene expression data. Bioinformatics 26, 139 (Jan. 1, 2010)). Gene expression values are expressed as log¬2¬(counts per million), abbreviated as log 2(CPM).

Molecular subtype association analysis: MARCO gene expression association analysis with molecular subtypes (Luminal A, Luminal B, HER2-enriched and Basal-like) was assessed using a linear model fitted by the LIMMA package (G K. Smyth, in Bioinformatics and Computational Biology Solutions Using R and Bioconductor, R. Gentleman, V. Carey, W. Huber, R. Irizarry, S. Dudoit, Eds. (Springer New York, 2005), pp. 397-420) for R (R Core Team. (2013)) using precision weights from Voom (C. W. Law, Y. Chen, W. Shi, G K. Smyth, voom: Precision weights unlock linear model analysis tools for RNA-seq read counts. Genome biology 15, R29 (2014)). In the linear model the MARCO gene expression was set as response variable and the predictors were factors representing the molecular subtypes with Luminal A as the reference level. The null hypothesis testing (two-sided) to determine the significance of estimated coefficients was based on the moderated t-statistic from the empirical Bayes method provided in the LIMMA package.

Gene-gene expression association analysis: Association between expression of MARCO and genes in "gene set 1" and "gene set 2" was assessed by linear modelling as well as correlation analysis. The linear model was fitted using the LIMMA package (G K. Smyth, in Bioinformatics and Computational Biology Solutions Using R and Bioconductor, R. Gentleman, V. Carey, W. Huber, R. Irizarry, S. Dudoit, Eds. (Springer New York, 2005), pp. 397-420) for R (R Core Team. (2013)) using precision weights from Voom (C. W. Law, Y. Chen, W. Shi, G K. Smyth, voom: Precision weights unlock linear model analysis tools for RNA-seq read counts. Genome biology 15, R29 (2014)). In the linear model, the gene of interest (in "gene set 1" or "gene set 2") was set as response variable with MARCO as predictor while also adjusting for molecular subtype. Null hypothesis testing (two-sided) to determine the significance of estimated coefficients was based on the moderated t-statistic from the empirical Bayes method provided in the LIMMA package. A rank-based gene set test was applied to assess if "gene set 1" or "gene set 2" were higher ranked relative randomly selected gene sets (J. Michaud et al., Integrative analysis of RUNX1 downstream pathways and target genes. BMC genomics 9, 363 (2008)). Marginal correlation between MARCO and genes in "gene set 1" and "gene set 2" was assessed by means of Spearman's rank correlation coefficient (rho) with p-values based on a two-sided test.

Example 2

In this example, two preclinical mouse tumor models, the 4T1 mammary carcinoma and the B16 melanoma models, were used to characterize the expression of MARCO in the TME and assess its role in tumor progression.

Using immunofluorescent staining, it was found that in the 4T1 mammary carcinoma, MARCO (left panel-red) was co-expressed on CD11b and F4/80 positive cells (merged right panel-magenta) (FIG. 1A). Likewise, in the B16 melanoma model MARCO$^+$ TAMs also stained positively for both CD11b and F4/80 (FIG. 1B left and right panels). Thus, TAMs, but not other cell types in the tumor stroma, expressed MARCO in these cancer models and localised near the tumor capsule (FIG. 5A).

To further dissect which subtype of TAMs expressed MARCO, CD45$^+$CD11b$^+$ TAMs from B16 tumors were sorted into four subpopulations based on their expression of Ly6C and MHCII (FIG. 1C). These represent inflammatory monocytes, immature macrophages, classically activated (M1) and alternatively activated (M2) macrophages, respectively (denoted as populations 1-4) (10). Using this categorization, M2 macrophages have been described to be immunosuppressive and tumor promoting in vivo (population 4), whereas M1 macrophages are inflammatory and can eradicate tumors (population 2) (4).

Next quantitative PCR (qPCR) was employed to further define the TAM populations with respect to MARCO expression. It was found that MARCO was most highly expressed in the Ly6C$^{low}$, MHCII$^{low}$ M2 subpopulation, which also expressed the M2 markers arg1 and retnla (fizz1) (FIG. 1D). The expression of MARCO on immunosuppressive M2 TAMs was further supported by in vitro polarization of bone marrow-derived macrophages using tumor supernatant or cytokines. MARCO was upregulated on M2 macrophages as well as on TAMs differentiated with supernatant from B16 melanoma cells (FIG. 1E). These in vitro-derived MARCO$^+$CD68$^+$ MHCII$^+$ Ly6C$^+$ expressing macrophages also co-expressed M2 markers such as CD115 and CD206 by FACS as well as arg1, retnla and chi3l3 as determined by qPCR (FIG. 1F-G).

Considering the fact that certain cytokines, such as IL-10 and TGF-β, are frequently overexpressed in the TME and can promote M2 polarization of macrophages, assays were carried out to study whether these cytokines could affect MARCO expression. Indeed, it was found that the upregulation of MARCO induced by the tumor supernatant could be mimicked by stimulation of a peritoneal macrophage cell line with IL-10 or TGF-β (FIGS. 5B-C). These data implicate MARCO expression on TAMs to the re-activation of EMT, which is driven by TGF-β and acts as a link between inflammation and cancer progression towards metastasis (11-13).

Example 3

In view of the restricted expression pattern of MARCO on tumor-promoting M2 TAMs, assays were carried out to assess whether MARCO could be used as a target for immunotherapy using an anti-MARCO specific antibody.

The anti-MARCO IgG had the ability to reach MARCO-expressing TAMs in the 4T1 mammary fat pad breast carcinoma model tumor (FIG. 2A and FIG. 6A). 4T1 tumor-bearing mice that were treated with anti-MARCO IgG (twice weekly) had smaller tumors measured as both tumor volume and weight compared to control mice (FIG. 2B). In addition, it was observed that treatment with anti-MARCO IgG significantly reduced metastatic spread to the lungs as determined by in vitro expansion of tumor cells from the lungs of the mice (FIG. 2C).

Furthermore, it was discovered that treatment with anti-MARCO IgG resulted in a shift in the composition of TAM populations in the TME of 4T1 tumors, with a reduction of monocytes, an increase in M1 TAMs and a concomitant decrease of the M2 TAM population (FIG. 2D).

To determine if this shift rendered the tumor more immunogenic, the draining lymph nodes were characterized. It was observed that there was increased germinal centre formation as well as altered CD4/CD8 T cell ratios with a tendency for reduction of regulatory T cells (FIGS. 2E-F). These data support an immunostimulatory effect of anti-MARCO treatment in this preclinical tumor model.

The 4T1 mammary tumor is a potent inducer of MDSCs which are a heterogeneous group of immature myeloid cells that suppress T cell activation and accumulate in the spleen during cancer (2, 14). Next, assays were carried out to explore the possibility that anti-MARCO treatment had affected this population of cells. However, no evidence could be found for changes in either the monocytic (M-MDSC) or polymorphonuclear (PMN-MDSC) subpopulations in the spleens of tumor bearing mice (FIG. 6B). In addition, no alterations were observed in other splenic lymphocyte populations including macrophages, B cells, T cells, NKT cells or NK cells (FIGS. 6C-E).

Example 4

To evaluate the generality of anti-MARCO immunotherapy and to further dissect its mechanism of action, assays were carried out to test its efficacy in the B16 melanoma model (FIG. 7A). To create a targetable stromal compartment B16 melanoma, cells expressing luciferase were injected subcutaneously in matrigel, treated with anti-MARCO mAb, and tumor growth was measured using an in vivo imaging system (FIG. 7B). As in the 4T1 mammary tumor model, the anti-MARCO antibody was injected intravenously to tumor bearing mice in which it reached MARCO$^+$ TAMs in the stroma (FIG. 3A). The treatment significantly reduced tumor growth over the 9 days of experimental observation (FIG. 3B). The TME displayed similar changes as were observed in the 4T1 model, with decreased numbers of immature macrophages, an altered CD4/CD8 ratio and decreased numbers of regulatory T cells, whereas no effect was evident for other lymphocytes or myeloid cells (FIGS. 7C-E).

The efficacy of anti-MARCO treatment was next compared with immunotherapies with known activity in this model. Briefly, groups of mice were injected with anti-MARCO alone or together with an antibody against the TRP1 antigen, which induces direct ADCC of the tumor (TA99 (15, 16)) or immune checkpoint therapy using anti-CTLA4 antibodies (17) (FIG. 3C). It was found that anti-MARCO treatment was as effective as TA99 or anti-CTLA4 in arresting tumor growth, and an additive effect was apparent when combining anti-MARCO with either TA99 or CTLA-4, respectively. In addition, there was no effect of the anti-MARCO treatment on tumor growth in MARCO$^{-/-}$ mice (FIG. 3C). Since previous experiments had shown that that anti-MARCO altered the TME and increased germinal centre formation, the therapy was investigated in combination with anti-CTLA4 treatment in a survival study. It was observed that anti-MARCO treatment significantly increased the overall survival alone, and also enhanced the anti-CTLA4 effect (FIG. 3D).

Example 5

Previous studies have indicated that anti-tumor antibodies require the engagement of distinct FcRs to either promote cytotoxicity (16) or to induce agonistic activity through crosslinking (18). To further dissect the mechanism through which engagement of anti-MARCO on TAMs resulted in alteration in the TME, anti-MARCO antibodies with defined Fc domains that selectively engaged murine FcRs were generated.

Using these Fc variants, the inventors determined that the antibody that was unable to bind FcRs had a diminished effect, suggesting involvement of Fc-receptors (FIG. 3G). Using Fc-receptor deficient mice lacking all Fc-receptors or only activating FcγRI, III and FcγRIV receptors (19, 20), the inventors found that the anti-MARCO effect was not dependent on activating receptors leaving only the inhibitory FcγRIIB to be responsible for the anti-tumor effect (FIG. 3E). To verify the involvement of FcγRIIB, the inventors also tested the ability of anti-MARCO to decrease tumor growth in FcγRIIB$^{-/-}$ mice and it was less effective (FIG. 3E). FcγRIIB engagement is required for the agonistic activity of antibodies targeting the TNFR superfamily members CD40 and DR5 (18) by facilitating crosslinking of these trimeric receptors. It is thus likely that the anti-tumor activity of the anti-MARCO antibody also results from crosslinking of this trimeric receptor to modify TAM activation or composition.

Example 6

To take a step towards immunotherapy in patients, the inventors next investigated the presence of MARCO$^+$ TAMs in human primary breast cancer biopsies. Using two different clinical cohorts, the inventors found that MARCO was most highly expressed in the basal (triple negative) subgroup of patients compared to in LumA, LumB and Her2$^+$ subgroups (21) (FIGS. 4A-B). This correlates with the findings of MARCO-expressing TAMs in mice, as the 4T1 tumor model is considered to represent human basal breast cancer (22).

Patients with the basal tumor subtype are also those with the poorest prognosis, and the current treatment options are limited to cytotoxic agents. To further evaluate MARCO expression in human breast tumors, the inventors compared it to the expression of defined M2 TAM markers (arg1, retnlb, il4r, chia, cd68 and cd163), including FcγRIIB MARCO expression correlated with all these genes, indicating that the receptor is expressed in cancers with high M2 TAM genetic signatures (FIGS. 4C-D).

The inventors correlated MARCO expression with a number of EMT markers (Table 1) and observed that many of these were co-upregulated with MARCO in the tumors (FIGS. 4E-F).

TABLE 1

| Abbreviation | Gene ID | Name | Function/Process |
|---|---|---|---|
| SOX10 | 6663 | SRY (sex determining region Y)-box 10 | embryonic development |
| GSC | 145258 | goosecoid homeobox | embryonic development |
| MMP9 | 4318 | matrix metallopeptidase 9 | ECM remodelling |
| VIM | 7431 | vimentin | attachment, migration, signalling |
| CDH1 | 999 | cadherin 1, type 1, E-cadherin (epithelial) | adhesion |
| CDH2 | 1000 | cadherin 2, type 1, N-cadherin (neuronal) | adhesion |
| MMP3 | 4314 | matrix metallopeptidase 3 | ECM remodelling |
| SNAI2 | 6591 | snail family zinc finger 2 | EMT, antiapoptotic |
| MMP2 | 4313 | matrix metallopeptidase 2 | ECM remodelling |
| SNAI1 | 6615 | snail family zinc finger 1 | embryonic development |
| ITGB6 | 3694 | integrin, beta 6 | adhesion |
| DSP | 1832 | desmoplakin | cell junctions |
| FOXC2 | 2303 | forkhead box C2 | embryonic development |
| TWIST1 | 7291 | twist family bHLH transcription factor 1 | differentiation |
| FN1 | 2335 | fibronectin 1 | adhesion, migration, metastasis |

Among these genes mmp9 is involved in tissue remodelling and metastasis (23), and snail as well as twist are considered master regulators of EMT (24). These data suggest that measuring MARCO could be a clinically relevant biomarker when evaluating basal mammary carcinomas.

Finally, the inventors stained human basal breast cancer tumor biopsies for the presence of MARCO and recorded its expression on CD68$^+$ TAMs in the tumor stroma (FIG. 4G). These data demonstrate that MARCO is a marker for TAMs in basal human breast cancer and pinpoint a group of patients that could benefit from anti-MARCO therapy. Not all macrophages in human basal breast tumors stained positively, indicating that a MARCO-expressing subtype of TAMs exists in human breast cancer, and further evaluation of this subtype for other cancers is warranted.

In summary, the inventors describe a novel approach using an antibody to selectively target a specific subtype of TAMs in the tumor stroma. This approach was sufficient to shift the anti-inflammatory, pro-tumorigenic and pro-metastatic TME to a more pro-inflammatory and less supportive TME for tumor progression. As a result, tumor growth and metastatic spread was inhibited. While targeting TAMs is an attractive alternative to tumor treatment, the only treatment modality to date that has shown promise is cytokine blockade, a pleiotropic approach that has limited applicability (25-27). CSF-1 blockade has been evaluated for both tumor treatment and in order to enhance the response to chemotherapy. This TAM-directed treatment also enhanced an anti-tumor effect mediated by anti-CTLA4 antibody therapy. Anti-CTLA4 treatment depends on the activating FcγRIV expression by macrophages (28), whereas the inventors find that potent anti-MARCO treatment depends on FcγRIIB expression, just as has been reported for anti-CD40 (18). The observed Fc-dependence as well as the further characterization of the MARCO-expressing TAM population is important aspects to take into consideration when designing anti-MARCO mAb therapeutics for the treatment of cancer beyond the case of basal breast carcinoma.

REFERENCES

1. P. Sharma, J. P. Allison, The future of immune checkpoint therapy. *Science* 348, 56 (Apr. 3, 2015).
2. S. Solito et al., Myeloid-derived suppressor cell heterogeneity in human cancers. *Ann N Y Acad Sci* 1319, 47 (June, 2014).
3. D. M. Mosser, J. P. Edwards, Exploring the full spectrum of macrophage activation. *Nat Rev Immunol* 8, 958 (December, 2008).
4. R. Noy, J. W. Pollard, Tumor-associated macrophages: from mechanisms to therapy. *Immunity* 41, 49 (Jul. 17, 2014).
5. R. A. Franklin et al., The cellular and molecular origin of tumor-associated macrophages. *Science* 344, 921 (May 23, 2014).
6. J. Fuxe, M. C. Karlsson, TGF-beta-induced epithelial-mesenchymal transition: a link between cancer and inflammation. *Seminars in cancer biology* 22, 455 (October, 2012).
7. N. Matsushita, H. Komine, A. Grolleau-Julius, S. Pilon-Thomas, J. J. Mule, Targeting MARCO can lead to enhanced dendritic cell motility and anti-melanoma activity. *Cancer Immunol Immunother* 59, 875 (June, 2010).
8. O. Elomaa et al., Cloning of a novel bacteria-binding receptor structurally related to scavenger receptors and expressed in a subset of macrophages. *Cell* 80, 603 (1995).
9. A. Bergamaschi et al., Extracellular matrix signature identifies breast cancer subgroups with different clinical outcome. *J Pathol* 214, 357 (February, 2008).
10. C. D. Mills, M1 and M2 Macrophages: Oracles of Health and Disease. *Crit Rev Immunol* 32, 463 (2012).
11. P. J. Miettinen, R. Ebner, A. R. Lopez, R. Derynck, TGF-beta induced transdifferentiation of mammary epithelial cells to mesenchymal cells: involvement of type I receptors. *J Cell Biol* 127, 2021 (December, 1994).
12. S. A. Mani et al., The epithelial-mesenchymal transition generates cells with properties of stem cells. *Cell* 133, 704 (May 16, 2008).
13. J. Fuxe, M. C. Karlsson, TGF-beta-induced epithelial-mesenchymal transition: a link between cancer and inflammation. *Semin Cancer Biol* 22, 455 (October, 2012).
14. P. Sinha, V. K. Clements, A. M. Fulton, S. Ostrand-Rosenberg, Prostaglandin E2 promotes tumor progression by inducing myeloid-derived suppressor cells. *Cancer Res* 67, 4507 (May 1, 2007).
15. T. M. Thomson, M. J. Mattes, L. Roux, L. J. Old, K. O. Lloyd, Pigmentation-associated glycoprotein of human melanomas and melanocytes: definition with a mouse monoclonal antibody. *J Invest Dermatol* 85, 169 (August, 1985).
16. R. Clynes, Y. Takechi, Y. Moroi, A. Houghton, J. V. Ravetch, Fc receptors are required in passive and active immunity to melanoma. *Proc Natl Acad Sci USA* 95, 652 (Jan. 20, 1998).
17. D. R. Leach, M. F. Krummel, J. P. Allison, Enhancement of antitumor immunity by CTLA-4 blockade. *Science* 271, 1734 (Mar. 22, 1996).
18. F. Li, J. V. Ravetch, Inhibitory Fcgamma receptor engagement drives adjuvant and anti-tumor activities of agonistic CD40 antibodies. *Science* 333, 1030 (Aug. 19, 2011).
19. P. Smith, D. J. DiLillo, S. Bournazos, F. Li, J. V. Ravetch, Mouse model recapitulating human Fcgamma receptor structural and functional diversity. *Proc Natl Acad Sci USA* 109, 6181 (Apr. 17, 2012).
20. T. Takai, M. Li, D. Sylvestre, R. Clynes, J. V. Ravetch, FcR gamma chain deletion results in pleiotrophic effector cell defects. *Cell* 76, 519 (Feb. 11, 1994).
21. T. Sorlie et al., Gene expression patterns of breast carcinomas distinguish tumor subclasses with clinical implications. *Proc Natl Acad Sci USA* 98, 10869 (Sep. 11, 2001).
22. P. Kaur et al., A mouse model for triple-negative breast cancer tumor-initiating cells (TNBC-TICs) exhibits similar aggressive phenotype to the human disease. *BMC Cancer* 12, 120 (2012).
23. M. Morini et al., The alpha 3 beta 1 integrin is associated with mammary carcinoma cell metastasis, invasion, and gelatinase B (MMP-9) activity. *Int J Cancer* 87, 336 (Aug. 1, 2000).
24. J. Xu, S. Lamouille, R. Derynck, TGF-beta-induced epithelial to mesenchymal transition. *Cell research* 19, 156 (February, 2009).
25. D. G. DeNardo et al., Leukocyte complexity predicts breast cancer survival and functionally regulates response to chemotherapy. *Cancer Discov* 1, 54 (June, 2011).
26. S. M. Pyonteck et al., CSF-1R inhibition alters macrophage polarization and blocks glioma progression. *Nat Med* 19, 1264 (October, 2013).
27. D. C. Strachan et al., CSF1R inhibition delays cervical and mammary tumor growth in murine models by attenuating the turnover of tumor-associated macrophages and enhancing infiltration by CD8 T cells. *Oncoimmunology* 2, e26968 (Dec. 1, 2013).
28. T. R. Simpson et al., Fc-dependent depletion of tumor-infiltrating regulatory T cells co-defines the efficacy of anti-CTLA-4 therapy against melanoma. *J Exp Med* 210, 1695 (Aug. 26, 2013).
29. D. M. Mosser, X. Zhang, Activation of murine macrophages. *Current protocols in immunology*/edited by John E. Coligan . . . [et al.] Chapter 14, Unit 14 2 (November, 2008).

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated by reference in their entireties.

What is claimed is:

1. An isolated antibody or an antigen-binding fragment thereof that specifically interacts and shows a measurable affinity to a macrophage receptor with collagenous structure (MARCO) epitope, comprising
   (i) a heavy chain comprising heavy chain CDRs 1-3 of SEQ ID NO: 3 and
   (ii) a light chain comprising light chain CDRs 1-3 of SEQ ID NO: 5,
   wherein the light chain differs from SEQ ID NO: 5 or the heavy chain differs from SEQ ID NO: 3.

2. The isolated antibody or an antigen-binding fragment thereof of claim 1, wherein the heavy chain CDRs 1-3 comprises the respective sequences of SEQ ID Nos: 30-32 and the light chain CDRs 1-3 comprises the respective sequences of SEQ ID Nos: 33-35.

3. The isolated antibody or an antigen-binding fragment thereof of claim 2, wherein the heavy chain comprises the sequence of SEQ ID No: 25.

4. The isolated antibody or an antigen-binding fragment thereof of claim 2, wherein the light chain comprises the sequence of SEQ ID No: 27 or 29.

5. The antibody or an antigen-binding fragment of claim 1, comprising an Fc region that binds to an inhibitory Fc-receptor.

6. The antibody or an antigen-binding fragment of claim 1, wherein said antibody is a chimeric antibody, a humanized antibody, or humanized monoclonal antibody.

7. A kit for detecting a macrophage receptor with collagenous structure (MARCO) epitope, comprising: (a) an antibody of claim 1 or a fragment thereof, capable of specifically binding in vitro to a macrophage receptor with collagenous structure (MARCO) epitope; and, (b) a reagent that binds, directly, or indirectly, to said antibody or the fragment thereof.

8. A pharmaceutical composition comprising the isolated antibody or antigen-binding fragment thereof of claim 1, and a pharmaceutically acceptable carrier.

* * * * *

SEQUENCE LISTING

<160> NUMBER OF SEQ ID NOS: 35

<210> SEQ ID NO 1
<211> LENGTH: 520
<212> TYPE: PRT
<213> ORGANISM: Homo sapiens

<400> SEQUENCE: 1

Met Arg Asn Lys Lys Ile Leu Lys Glu Asp Glu Leu Leu Ser Glu Thr
1               5                   10                  15

Gln Gln Ala Ala Phe His Gln Ile Ala Met Glu Pro Phe Glu Ile Asn
            20                  25                  30

Val Pro Lys Pro Lys Arg Arg Asn Gly Val Asn Phe Ser Leu Ala Val
        35                  40                  45

Val Val Ile Tyr Leu Ile Leu Leu Thr Ala Gly Ala Gly Leu Leu Val
    50                  55                  60

Val Gln Val Leu Asn Leu Gln Ala Arg Leu Arg Val Leu Glu Met Tyr
65                  70                  75                  80

Phe Leu Asn Asp Thr Leu Ala Ala Glu Asp Ser Pro Ser Phe Ser Leu
                85                  90                  95

Leu Gln Ser Ala His Pro Gly Glu His Leu Ala Gln Gly Ala Ser Arg
            100                 105                 110

Leu Gln Val Leu Gln Ala Gln Leu Thr Trp Val Arg Val Ser His Glu
        115                 120                 125

His Leu Leu Gln Arg Val Asp Asn Phe Thr Gln Asn Pro Gly Met Phe
    130                 135                 140

Arg Ile Lys Gly Glu Gln Gly Ala Pro Gly Leu Gln Gly His Lys Gly
145                 150                 155                 160

Ala Met Gly Met Pro Gly Ala Pro Gly Pro Gly Pro Pro Ala Glu
                165                 170                 175

Lys Gly Ala Lys Gly Ala Met Gly Arg Asp Gly Ala Thr Gly Pro Ser
            180                 185                 190

Gly Pro Gln Gly Pro Pro Gly Val Lys Gly Glu Ala Gly Leu Gln Gly
        195                 200                 205

Pro Gln Gly Ala Pro Gly Lys Gln Gly Ala Thr Gly Thr Pro Gly Pro
    210                 215                 220

Gln Gly Glu Lys Gly Ser Lys Gly Asp Gly Gly Leu Ile Gly Pro Lys
225                 230                 235                 240

Gly Glu Thr Gly Thr Lys Gly Glu Lys Gly Asp Leu Gly Leu Pro Gly
                245                 250                 255

Ser Lys Gly Asp Arg Gly Met Lys Gly Asp Ala Gly Val Met Gly Pro
            260                 265                 270

Pro Gly Ala Gln Gly Ser Lys Gly Asp Phe Gly Arg Pro Gly Pro Pro
        275                 280                 285

Gly Leu Ala Gly Phe Pro Gly Ala Lys Gly Asp Gln Gly Gln Pro Gly
    290                 295                 300

Leu Gln Gly Val Pro Gly Pro Gly Ala Val Gly His Pro Gly Ala
305                 310                 315                 320

Lys Gly Glu Pro Gly Ser Ala Gly Ser Pro Gly Arg Ala Gly Leu Pro
                325                 330                 335

Gly Ser Pro Gly Ser Pro Gly Ala Thr Gly Leu Lys Gly Ser Lys Gly
            340                 345                 350

Asp Thr Gly Leu Gln Gly Gln Gln Gly Arg Lys Gly Glu Ser Gly Val
        355                 360                 365

```
Pro Gly Pro Ala Gly Val Lys Gly Glu Gln Gly Ser Pro Gly Leu Ala
    370                 375                 380
Gly Pro Lys Gly Ala Pro Gly Gln Ala Gly Gln Lys Gly Asp Gln Gly
385                 390                 395                 400
Val Lys Gly Ser Ser Gly Glu Gln Gly Val Lys Gly Glu Lys Gly Glu
                405                 410                 415
Arg Gly Glu Asn Ser Val Ser Val Arg Ile Val Gly Ser Ser Asn Arg
                420                 425                 430
Gly Arg Ala Glu Val Tyr Tyr Ser Gly Thr Trp Gly Thr Ile Cys Asp
            435                 440                 445
Asp Glu Trp Gln Asn Ser Asp Ala Ile Val Phe Cys Arg Met Leu Gly
        450                 455                 460
Tyr Ser Lys Gly Arg Ala Leu Tyr Lys Val Gly Ala Gly Thr Gly Gln
465                 470                 475                 480
Ile Trp Leu Asp Asn Val Gln Cys Arg Gly Thr Glu Ser Thr Leu Trp
                485                 490                 495
Ser Cys Thr Lys Asn Ser Trp Gly His His Asp Cys Ser His Glu Glu
                500                 505                 510
Asp Ala Gly Val Glu Cys Ser Val
            515                 520

<210> SEQ ID NO 2
<211> LENGTH: 801
<212> TYPE: DNA
<213> ORGANISM: Rattus rattus

<400> SEQUENCE: 2 ggggggggggg ggataagatc actgtcctct ctacagtcac tgagtacaaa ggacctcacc     60
atgggatgga tctgtatcat ctttcttgtg caacagcta caggtgtcct ccccccaggtc    120
aagctgctgc agtctggggc tgcattggtg aagcctggag cctctgtgaa gatgtcttgc    180
aaagcttctg gttatacatt cactgactac tgggtgagct gggtgaagca gagtcatgga    240
aagagccttg agtgcattgg ggaaatttct cctaacagtg gtactactaa cttcaatgaa    300
aagttcaagg gcaaggccac attgactgta gacaaatcca ccagcacagc ctatatggag    360
ctcagcagat tgacatctga ggactctgca atctattact gtacaagatg caggtatact    420
accggagtcc attactttga ttactggggc caaggagtca tggtcacagt ctcctcagct    480
gaaacaacag ccccatctgt ctatccactg gctcctggaa ctgctctcaa agtaactcc    540
atggtgaccc tgggatgcct ggtcaagggc tatttccctg agccagtcac cgtgacctgg    600
aactctggag ccctgtccag cggtgtgcac accttcccag ctgtcctgca gtctgggctc    660
tacactctca ccagctcagt gactgtaccc tccagcacct ggcccagcca gaccgtcacc    720
tgcaacgtag cccacccggc cagcagcacc aaggtggaca gaaaattga aagggcgaa     780
ttcgcaacct acatggccgc c                                               801

<210> SEQ ID NO 3
<211> LENGTH: 267
<212> TYPE: PRT
<213> ORGANISM: Rattus rattus

<400> SEQUENCE: 3

Gly Gly Gly Gly Ile Arg Ser Leu Ser Ser Leu Gln Ser Leu Ser Thr
1               5                   10                  15
Lys Asp Leu Thr Met Gly Trp Ile Cys Ile Ile Phe Leu Val Ala Thr
                20                  25                  30
```

Ala Thr Gly Val Leu Pro Gln Val Lys Leu Leu Gln Ser Gly Ala Ala
            35                  40                  45

Leu Val Lys Pro Gly Ala Ser Val Lys Met Ser Cys Lys Ala Ser Gly
 50                  55                  60

Tyr Thr Phe Thr Asp Tyr Trp Val Ser Trp Val Lys Gln Ser His Gly
 65                  70                  75                  80

Lys Ser Leu Glu Cys Ile Gly Glu Ile Ser Pro Asn Ser Gly Thr Thr
                 85                  90                  95

Asn Phe Asn Glu Lys Phe Lys Gly Lys Ala Thr Leu Thr Val Asp Lys
                100                 105                 110

Ser Thr Ser Thr Ala Tyr Met Glu Leu Ser Arg Leu Thr Ser Glu Asp
            115                 120                 125

Ser Ala Ile Tyr Tyr Cys Thr Arg Cys Arg Tyr Thr Thr Gly Val His
        130                 135                 140

Tyr Phe Asp Tyr Trp Gly Gln Gly Val Met Val Thr Val Ser Ser Ala
145                 150                 155                 160

Glu Thr Thr Ala Pro Ser Val Tyr Pro Leu Ala Pro Gly Thr Ala Leu
                165                 170                 175

Lys Ser Asn Ser Met Val Thr Leu Gly Cys Leu Val Lys Gly Tyr Phe
            180                 185                 190

Pro Glu Pro Val Thr Val Thr Trp Asn Ser Gly Ala Leu Ser Ser Gly
        195                 200                 205

Val His Thr Phe Pro Ala Val Leu Gln Ser Gly Leu Tyr Thr Leu Thr
    210                 215                 220

Ser Ser Val Thr Val Pro Ser Ser Thr Trp Pro Ser Gln Thr Val Thr
225                 230                 235                 240

Cys Asn Val Ala His Pro Ala Ser Ser Thr Lys Val Asp Lys Lys Ile
                245                 250                 255

Glu Lys Gly Glu Phe Ala Thr Tyr Met Ala Ala
            260                 265

<210> SEQ ID NO 4
<211> LENGTH: 772
<212> TYPE: DNA
<213> ORGANISM: Rattus rattus

<400> SEQUENCE: 4
gggggggggg gggtgattcc acttctaatt tcatctcctc aaaacgatga gtcctgccag    60
tccctgtttt tattattgct ttggattctg ggaaccaaag gtgatgttgt gctgacccag   120
actccatcca tattgtctgt taccattgga caatcggtct ccatctcttg caggtcaagt   180
cagagtctct tagatagtga tggaaacagc tatttatatt ggttcctaca gaggccaggc   240
cagtctccac agcgtctaat ttatttggta tccaatttgg gatctggggt ccccaacagg   300
ttcagtggca gtgggtcagg aacagattc acactcaaaa tcagtggagt ggaggctgag   360
gatttgggag tttattactg catgcaagct acccatgctc cgtggacgtt cggtggaggc   420
accaagctgg aattgaaacg ggctgatgct gcaccaactg tatctatctt cccaccatcc   480
acggaacagt tagcaactgg aggtgcctca gtcgtgtgcc tcatgaacaa cttctatccc   540
agagacatca gtgtcaagtg gaagattgat ggcactgaac gacgagatgg tgtcctggac   600
agtgttactg atcaggacag caaagacagc acgtacagca tgagcagcac cctctcgttg   660
accaaggctg actatgaaag tcataacctc tatacctgtg aggttgttca taaacatcat   720
cctcacccag ggcgaattcc agcaactggc gcttactagg gccgaccgcc ag           772

<210> SEQ ID NO 5
<211> LENGTH: 252
<212> TYPE: PRT
<213> ORGANISM: Rattus rattus

<400> SEQUENCE: 5

Gly Gly Gly Gly Val Ile Pro Leu Leu Ile Ser Ser Pro Gln Asn Asp
1               5                   10                  15

Glu Ser Cys Gln Ser Leu Phe Leu Leu Leu Trp Ile Leu Gly Thr
            20                  25                  30

Lys Gly Asp Val Val Leu Thr Gln Thr Pro Ser Ile Leu Ser Val Thr
        35                  40                  45

Ile Gly Gln Ser Val Ser Ile Ser Cys Arg Ser Ser Gln Ser Leu Leu
    50                  55                  60

Asp Ser Asp Gly Asn Ser Tyr Leu Tyr Trp Phe Leu Gln Arg Pro Gly
65                  70                  75                  80

Gln Ser Pro Gln Arg Leu Ile Tyr Leu Val Ser Asn Leu Gly Ser Gly
                85                  90                  95

Val Pro Asn Arg Phe Ser Gly Ser Gly Ser Gly Thr Asp Phe Thr Leu
            100                 105                 110

Lys Ile Ser Gly Val Glu Ala Glu Asp Leu Gly Val Tyr Tyr Cys Met
        115                 120                 125

Gln Ala Thr His Ala Pro Trp Thr Phe Gly Gly Gly Thr Lys Leu Glu
    130                 135                 140

Leu Lys Arg Ala Asp Ala Ala Pro Thr Val Ser Ile Phe Pro Pro Ser
145                 150                 155                 160

Thr Glu Gln Leu Ala Thr Gly Gly Ala Ser Val Val Cys Leu Met Asn
                165                 170                 175

Asn Phe Tyr Pro Arg Asp Ile Ser Val Lys Trp Lys Ile Asp Gly Thr
            180                 185                 190

Glu Arg Arg Asp Gly Val Leu Asp Ser Val Thr Asp Gln Asp Ser Lys
        195                 200                 205

Asp Ser Thr Tyr Ser Met Ser Ser Thr Leu Ser Leu Thr Lys Ala Asp
    210                 215                 220

Tyr Glu Ser His Asn Leu Tyr Thr Cys Glu Val Val His Lys His His
225                 230                 235                 240

Pro His Pro Gly Arg Ile Pro Ala Thr Gly Ala Tyr
                245                 250

<210> SEQ ID NO 6
<211> LENGTH: 21
<212> TYPE: DNA
<213> ORGANISM: Artificial Sequence
<220> FEATURE:
<223> OTHER INFORMATION: primer

<400> SEQUENCE: 6
ccacagtctg gcagttggaa g                                            21

<210> SEQ ID NO 7
<211> LENGTH: 22
<212> TYPE: DNA
<213> ORGANISM: Artificial Sequence
<220> FEATURE:
<223> OTHER INFORMATION: primer

<400> SEQUENCE: 7

```
ggttgtcagg ggagtgttga tg                                              22

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
tttgctttct gaaggggca                                                  20

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
tgggttctcc acctcttcat                                                 20

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
tttgctttct gaaggggca                                                  20

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
tcgcccatga actggtacac                                                 20

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
gccactgagg tctgggatgc                                                 20

<210> SEQ ID NO 13
<211> LENGTH: 21
<212> TYPE: DNA
<213> ORGANISM: Artificial Sequence
<220> FEATURE:
<223> OTHER INFORMATION: primer

<400> SEQUENCE: 13
tccttgagcc actgagcctt c                                               21

<210> SEQ ID NO 14
<211> LENGTH: 20
<212> TYPE: DNA
<213> ORGANISM: Artificial Sequence
```

```
<220> FEATURE:
<223> OTHER INFORMATION: primer

<400> SEQUENCE: 14
ggcaccccaa gggagacaaa                                                  20

<210> SEQ ID NO 15
<211> LENGTH: 17
<212> TYPE: DNA
<213> ORGANISM: Artificial Sequence
<220> FEATURE:
<223> OTHER INFORMATION: primer

<400> SEQUENCE: 15
tcccttcatg ccatgtc                                                     17

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
gaggtcgggt ggaagtacca                                                  20

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
tgcatcttgg ccttttcctt                                                  20

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18
ctgaggctga gaatacgatc                                                  20

<210> SEQ ID NO 19
<211> LENGTH: 20
<212> TYPE: DNA
<213> ORGANISM: Artificial Sequence
<220> FEATURE:
<223> OTHER INFORMATION: primer

<400> SEQUENCE: 19
gtggatcgat agcagaagag                                                  20

<210> SEQ ID NO 20
<211> LENGTH: 19
<212> TYPE: DNA
<213> ORGANISM: Artificial Sequence
<220> FEATURE:
<223> OTHER INFORMATION: primer

<400> SEQUENCE: 20
cgaaacgctt cacttccaa                                                   19
```

-continued

<210> SEQ ID NO 21
<211> LENGTH: 21
<212> TYPE: DNA
<213> ORGANISM: Artificial Sequence
<220> FEATURE:
<223> OTHER INFORMATION: primer

<400> SEQUENCE: 21
tgagcctata ttgctgtggc t                                          21

<210> SEQ ID NO 22
<211> LENGTH: 34
<212> TYPE: DNA
<213> ORGANISM: Artificial Sequence
<220> FEATURE:
<223> OTHER INFORMATION: Illumina adapter 1

<400> SEQUENCE: 22
agatcggaag agcacacgtc tgaactccag tcac                            34

<210> SEQ ID NO 23
<211> LENGTH: 17
<212> TYPE: DNA
<213> ORGANISM: Artificial Sequence
<220> FEATURE:
<223> OTHER INFORMATION: Illumina adapter 2

<400> SEQUENCE: 23
agatcggaag agcgtcg                                               17

<210> SEQ ID NO 24
<211> LENGTH: 427
<212> TYPE: DNA
<213> ORGANISM: Rattus rattus

<400> SEQUENCE: 24
gaattccacc atgggatgga tctgtatcat ctttcttgtg gcaacagcta caggtgtcct    60
ctcccaggtc aagctgctgc agtctggggc tgcattggtg aagcctggag cctctgtgaa   120
gatgtcttgc aaagcttctg gttatacatt cactgactac tgggtgagct gggtgaagca   180
gagtcatgga aagagccttg agtgcattgg ggaaatttct cctaacagtg gtactactaa   240
cttcaatgaa aagttcaagg gcaaggccac attgactgta gacaaatcca ccagcacagc   300
ctatatggag ctcagcagat tgacatctga ggactctgca atctattact gtacaagatg   360
caggtatact accggagtcc attactttga ttactggggc caaggagtca tggtcacagt   420
ctcgagc                                                            427

<210> SEQ ID NO 25
<211> LENGTH: 143
<212> TYPE: PRT
<213> ORGANISM: Rattus rattus

<400> SEQUENCE: 25

Asn Ser Thr Met Gly Trp Ile Cys Ile Ile Phe Leu Val Ala Thr Ala
1               5                   10                  15

Thr Gly Val Leu Ser Gln Val Lys Leu Leu Gln Ser Ser Gly Ala Ala
            20                  25                  30

Leu Val Lys Pro Gly Ala Ser Val Lys Met Ser Cys Lys Ala Ser Gly
        35                  40                  45

Tyr Thr Phe Thr Asp Tyr Trp Val Ser Trp Val Lys Gln Ser His Gly
    50                  55                  60

```
Lys Ser Leu Glu Cys Ile Gly Glu Ile Ser Pro Asn Ser Gly Thr Thr
 65                  70                  75                  80

Asn Phe Asn Glu Lys Phe Lys Gly Lys Ala Thr Leu Thr Val Asp Lys
                 85                  90                  95

Ser Thr Ser Thr Ala Tyr Met Glu Leu Ser Arg Leu Thr Ser Glu Asp
            100                 105                 110

Ser Ala Ile Tyr Tyr Cys Thr Arg Cys Arg Tyr Thr Thr Gly Val His
        115                 120                 125

Tyr Phe Asp Tyr Trp Gly Gln Gly Val Met Val Thr Val Ser Ser
    130                 135                 140
```

<210> SEQ ID NO 26
<211> LENGTH: 406
<212> TYPE: DNA
<213> ORGANISM: Homo sapiens

<400> SEQUENCE: 26

```
gaattccacc atgagtcctg tccagtccct gttttattta ttgctttgga ttctgggaac    60
caaaggtgat gttgtgctga cccagactcc atccatattg tctgttacca ttggacaatc   120
ggtctccatc tcttgcaggt caagtcagag tctcttagat agtgatggaa acagctattt   180
atattggttc ctacagaggc caggccagtc tccacagcgt ctaatttatt tggtatccaa   240
tttgggatct ggggtcccca acaggttcag tggcagtggg tcaggaacag atttcacact   300
caaaatcagt ggagtggagg ctgaggattt gggagtttat tactgcatgc aagctaccca   360
tgctccgtgg acgttcggtg gaggcaccaa gctggaattg aaacga               406
```

<210> SEQ ID NO 27
<211> LENGTH: 135
<212> TYPE: PRT
<213> ORGANISM: Homo sapiens

<400> SEQUENCE: 27

```
Asn Ser Thr Met Ser Pro Val Gln Ser Leu Phe Leu Leu Leu Leu Trp
  1               5                  10                  15

Ile Leu Gly Thr Lys Gly Asp Val Val Leu Thr Gln Thr Pro Ser Ile
                 20                  25                  30

Leu Ser Val Thr Ile Gly Gln Ser Val Ser Ile Ser Cys Arg Ser Ser
             35                  40                  45

Gln Ser Leu Leu Asp Ser Asp Gly Asn Ser Tyr Leu Tyr Trp Phe Leu
 50                  55                  60

Gln Arg Pro Gly Gln Ser Pro Gln Arg Leu Ile Tyr Leu Val Ser Asn
 65                  70                  75                  80

Leu Gly Ser Gly Val Pro Asn Arg Phe Ser Gly Ser Gly Ser Gly Thr
                 85                  90                  95

Asp Phe Thr Leu Lys Ile Ser Gly Val Glu Ala Glu Asp Leu Gly Val
            100                 105                 110

Tyr Tyr Cys Met Gln Ala Thr His Ala Pro Trp Thr Phe Gly Gly Gly
        115                 120                 125

Thr Lys Leu Glu Leu Lys Arg
    130                 135
```

<210> SEQ ID NO 28
<211> LENGTH: 406
<212> TYPE: DNA
<213> ORGANISM: Mus musculus

<400> SEQUENCE: 28

```
gaattccacc atgagtcctg tccagtccct gtttttatta ttgctttgga ttctgggaac    60
caaaggtgat gttgtgctga cccagactcc atccatattg tctgttacca ttggacaatc   120
ggtctccatc tcttgcaggt caagtcagag tctcttagat agtgatggaa acagctattt   180
atattggttc ctacagaggc caggccagtc tccacagcgt ctaatttatt tggtatccaa   240
tttgggatct ggggtcccca acaggttcag tggcagtggg tcaggaacag atttcacact   300
caaaatcagt ggagtggagg ctgaggattt gggagtttat tactgcatgc aagctaccca   360
tgctccgtgg acgttcggtg aggcaccaa gctggaattg aaacgg                   406
```

<210> SEQ ID NO 29
<211> LENGTH: 135
<212> TYPE: PRT
<213> ORGANISM: Mus musculus

<400> SEQUENCE: 29

```
Asn Ser Thr Met Ser Pro Val Gln Ser Leu Phe Leu Leu Leu Trp
1               5                   10                  15

Ile Leu Gly Thr Lys Gly Asp Val Val Leu Thr Gln Thr Pro Ser Ile
            20                  25                  30

Leu Ser Val Thr Ile Gly Gln Ser Val Ser Ile Ser Cys Arg Ser Ser
        35                  40                  45

Gln Ser Leu Leu Asp Ser Asp Gly Asn Ser Tyr Leu Tyr Trp Phe Leu
    50                  55                  60

Gln Arg Pro Gly Gln Ser Pro Gln Arg Leu Ile Tyr Leu Val Ser Asn
65                  70                  75                  80

Leu Gly Ser Gly Val Pro Asn Arg Phe Ser Gly Ser Gly Ser Gly Thr
                85                  90                  95

Asp Phe Thr Leu Lys Ile Ser Gly Val Glu Ala Glu Asp Leu Gly Val
            100                 105                 110

Tyr Tyr Cys Met Gln Ala Thr His Ala Pro Trp Thr Phe Gly Gly Gly
        115                 120                 125

Thr Lys Leu Glu Leu Lys Arg
    130                 135
```

<210> SEQ ID NO 30
<211> LENGTH: 8
<212> TYPE: PRT
<213> ORGANISM: Rattus rattus

<400> SEQUENCE: 30

```
Gly Tyr Thr Phe Thr Asp Tyr Trp
1               5
```

<210> SEQ ID NO 31
<211> LENGTH: 8
<212> TYPE: PRT
<213> ORGANISM: Rattus rattus

<400> SEQUENCE: 31

```
Ile Ser Pro Asn Ser Gly Thr Thr
1               5
```

<210> SEQ ID NO 32
<211> LENGTH: 14
<212> TYPE: PRT
<213> ORGANISM: Rattus rattus

```
<400> SEQUENCE: 32

Thr Arg Cys Arg Tyr Thr Thr Gly Val His Tyr Phe Asp Tyr
1               5                   10

<210> SEQ ID NO 33
<211> LENGTH: 12
<212> TYPE: PRT
<213> ORGANISM: Rattus rattus

<400> SEQUENCE: 33

Ser Gln Ser Leu Leu Asp Ser Asp Gly Asn Ser Tyr
1               5                   10

<210> SEQ ID NO 34
<211> LENGTH: 3
<212> TYPE: PRT
<213> ORGANISM: Rattus rattus

<400> SEQUENCE: 34

Leu Val Ser
1

<210> SEQ ID NO 35
<211> LENGTH: 9
<212> TYPE: PRT
<213> ORGANISM: Rattus rattus

<400> SEQUENCE: 35

Met Gln Ala Thr His Ala Pro Trp Thr
1               5
```